United States Patent [19]

Kohama et al.

[11] Patent Number: 5,597,727

[45] Date of Patent: Jan. 28, 1997

[54] CORYNEFORM BACTERIA DNA FRAGMENT CONTAINING A GENE RESPONSIBLE FOR THE FUNCTION OF AUTONOMOUS REPLICATION OF PLASMID

[75] Inventors: Keiko Kohama; Kazuhisa Hatakeyama; Yasurou Kurusu; Hideaki Yukawa, all of Inashiki-gun, Japan

[73] Assignee: Mitsubishi Chemical Corporation, Tokyo, Japan

[21] Appl. No.: 245,688

[22] Filed: May 18, 1994

[30]   Foreign Application Priority Data

May 20, 1993 [JP]   Japan .................................. 5-118397

[51] Int. Cl.⁶ .................... C07H 21/04; C12N 15/00; C12N 15/74; C12N 15/77

[52] U.S. Cl. ................... 435/252.32; 435/172.1; 435/172.3; 435/320.1; 435/840; 435/843; 536/23.1

[58] Field of Search ................ 536/23.1; 435/320.1, 435/252.32, 41, 108, 69.1, 71.1, 71.2, 91.1, 91.4, 243, 840, 843, 172.1, 172.3

[56]   References Cited

U.S. PATENT DOCUMENTS 4,703,012  10/1987  Boros et al. ..................... 435/320.1

4,874,698  10/1989  Ozaki et al. ..................... 435/108
4,946,781  8/1990   Nakamori et al. ................ 435/115
5,185,262  2/1993   Kohama et al. .................. 435/320.1

FOREIGN PATENT DOCUMENTS 0352763  1/1990  European Pat. Off. .

*Primary Examiner*—John L. LeGuyader
*Assistant Examiner*—Thomas G. Larson
*Attorney, Agent, or Firm*—Oblon, Spivak, McClelland, Maier, & Neustadt, P.C.

[57]   ABSTRACT

The present invention relates to a DNA fragment which contains a gene responsible for the function of autonomous replication of plasmid in a Coryneform bacterium, said gene being obtained from plasmid pBY503 held in *Brevibacterium stationis*, and in which at least one point mutation capable of increasing the copy number of plasmid exists on said gene region. By using a Coryneform transformed with the vector constructed using said DNA fragment and an industrially useful gene such as aspartase gene or tryptophan synthase gene, production of the useful product occurs with higher efficiency than conventional methods.

4 Claims, 1 Drawing Sheet

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1897 base pairs
        ( B ) TYPE: nucleic acid
        ( C ) STRANDEDNESS: double
        ( D ) TOPOLOGY: linear ( i i ) MOLECULE TYPE: plasmid DNA ( v i ) ORIGINAL SOURCE:
        ( A ) ORGANISM: Brevibacterium flavum
        ( B ) STRAIN: MJ233 COP1-1.8

( i x ) FEATURE:
        ( A ) NAME/KEY: peptide
        ( B ) LOCATION: 922..1704
        ( C ) IDENTIFICATION METHOD: experiment ( x i ) SEQUENCE DESCRIPTION: SEQ ID NO:1:

```
GCGCAGCCTG ACCATGGACA TGCTTCTACG TTCTTCCACA CTGGTATCTT TTGGTTGCAA      60

TATATATTGC AACCATGCTG GTAAAACAAC TTTTTAGCGT GTCTTGCCCA AAATTACAGT     120

CATGTGATTT ACAGTTGAAA GATACTGAAA ATCAAAGAAG GCCACTCGGC GGCAACCGAA     180

TGACCTTCGC TTATCACCCA GTCCTACCTG GGAGAAAGCA TGTACATGAT TATACCCAAT     240

AGTACGCCCG CGTACCCCAT TTCCGGTTCG CGTGTTAACA CGCCATCACG TTTGCGCCCT     300

GACTGCGCAG GCCTTGATGA CACCCCAGCG AGCACCGTTG ACCGGGACAA GCTGCTCGCA     360

CATCTTGGCC GTACAGCACT GCACGGGTCT ATAAGTCGAA ACTTCAAAGG CGCTTATCGC     420

CTCGTTGTGG ATAAGGAAAC GGGGGAAAAG CGAAGCGTTC CGAACCTTTA CCGCATTGAT     480

TCCGAAAAAC TCGGTCGCTG CGAATACGTC ATGCTGACTA GTAAGCAATA TGCTTCGGTC     540

ATGGTCATAG ACGTTGACCA GATAGGAGAG GCTGGAGGAC ATCCAGAAAA CCTCAACTCC     600

TATGTCAAAG GCGTTATCTG GGTACTTGTG CAGCACGGAA TTGGACCAGC ATGGGCAGGC     660

ATTAATCCGA TTAGTGGTAA AGCGCAGTTT ATTTGGCTTA TTGACCCAGT TTATGCAGGA     720

AAGAATCGTG CGTCCCGGAA TATGGAGCTA CTCAAAGCCA CAAGTCACGA GTTGGGTGAG     780

TTACTGGATC ATGATCCACA TTTTGCGCAT CGGTTTAGCC GGAGTCCTTT TTATACTGGA     840

AAGTCACCGG AGGCTTATCG CTGGTATTGC CAGCATGACC GGGTTATACG CCTCCAAGAC     900

TTTCTAAGGC AGGTGCGCGA G ATG GCG GGA CAA TCC CAG CAC ATT AAA AAC       951
                       Met Ala Gly Gln Ser Gln His Ile Lys Asn
                        1               5                   10

AAG CGC CAG CAA TTT AAC AGT GGC CGT GAG CTT ATT AAT GCG GTC AAA       999
Lys Arg Gln Gln Phe Asn Ser Gly Arg Glu Leu Ile Asn Ala Val Lys
              15                  20                  25

ACT CGC CGT GAA GAA GCC CAA GCC TTT AAA GCA CTT GCT GAG GAT GTC      1047
Thr Arg Arg Glu Glu Ala Gln Ala Phe Lys Ala Leu Ala Glu Asp Val
         30                  35                  40

GAA AAC GAG ATA AGT GAA GAA ATC GAT CAA TAC GAC CCG GAA CTA ATC      1095
Glu Asn Glu Ile Ser Glu Glu Ile Asp Gln Tyr Asp Pro Glu Leu Ile
         45                  50                  55

GAC GGG GTG CGC GTG CGC TGG ATT AGC CAA GGG GTC GCA GCA CGC GAC      1143
Asp Gly Val Arg Val Arg Trp Ile Ser Gln Gly Val Ala Ala Arg Asp
         60                  65                  70

GAA ACA GCG TTT AGC CAC GCA CTA AAA ATT GGT CAC CGC CTA CGC AAA      1191
```

| | | | | | | | | | | | | | | | | |
|---|---|---|---|---|---|---|---|---|---|---|---|---|---|---|---|---|
| Glu | Thr | Ala | Phe | Ser | His | Ala | Leu | Lys | Ile | Gly | His | Arg | Leu | Arg | Lys | |
| 75 | | | | 80 | | | | | 85 | | | | | 90 | | |

```
GCA GGA CAA CGA CTC ACA GAC GCC GCC GTT ATC GAT GCC TAC GAG CAT       1239
Ala Gly Gln Arg Leu Thr Asp Ala Ala Val Ile Asp Ala Tyr Glu His
             95              100                 105

GCC TAT AAC GTT GCA CAA CAA CAA GGC TCA GCA GGC CGA GAC AGC GAA       1287
Ala Tyr Asn Val Ala Gln Gln Gln Gly Ser Ala Gly Arg Asp Ser Glu
            110             115                 120

ATG CCA CCC ATG CGT GAC CAC CAG ACC ATG GCA CGA CGC GTA CGC GGC       1335
Met Pro Pro Met Arg Asp His Gln Thr Met Ala Arg Arg Val Arg Gly
        125             130                 135

TAT GTC ACC CAA TCC AAA ACC AAC ACA AGT CTA GGA GCT AGC GCT CCC       1383
Tyr Val Thr Gln Ser Lys Thr Asn Thr Ser Leu Gly Ala Ser Ala Pro
        140             145             150

GGA CGC GTT ACC AGC AGC GAA CGC AAA GCA CTG GCC ACC ATG GGG CGA       1431
Gly Arg Val Thr Ser Ser Glu Arg Lys Ala Leu Ala Thr Met Gly Arg
155             160             165                 170

AAA GGC GGA CAG AAA GCA GCA CAA CGC TGG AAA ACC GAT CCA GAA GGT       1479
Lys Gly Gly Gln Lys Ala Ala Gln Arg Trp Lys Thr Asp Pro Glu Gly
                175             180                 185

CAA TAC GCA CAA AAT CAG CTG CAG AAA CTA AAG AAA ACG CAC CGG AAG       1527
Gln Tyr Ala Gln Asn Gln Leu Gln Lys Leu Lys Lys Thr His Arg Lys
            190             195                 200

AAG CGG GTG GAA GGA CAG ACC ACG CGT GCG AAG ATT CAA GCC TTA ATT       1575
Lys Arg Val Glu Gly Gln Thr Thr Arg Ala Lys Ile Gln Ala Leu Ile
        205             210                 215

GGT GAA GCT TAC GTG CAA ACA GGC GAG GTA CTT ACC CGC AAA CAG ATT       1623
Gly Glu Ala Tyr Val Gln Thr Gly Glu Val Leu Thr Arg Lys Gln Ile
        220             225                 230

GTG GAT GAG ACA GGA CTA TCT AGA GCT ACA GTG ACA CGG CAT TTG GCG       1671
Val Asp Glu Thr Gly Leu Ser Arg Ala Thr Val Thr Arg His Leu Ala
235             240             245                 250

GCA CTT CGA GAA CAG GGA GCA CTT CCG GAA ACG TAGGGGCTCA TACCGTAAGC     1724
Ala Leu Arg Glu Gln Gly Ala Leu Pro Glu Thr
            255             260

AATATACGGT TCCCCTGCCG GTAGGAATGT AGTAATAACC TCTCTTGAAG AAAACCTTGT     1784

AGGGCAAGGC TACTTATGCT TCCGGGGTTA GTCGTTCTTC TATTGCGGTG ATGAGTTCTA     1844

GACCTTTATC TAAGTCCTGG GGGCTGCTGT TGCCGTGCGA GGCTTTGCTG CGC           1897
```

( 2 ) INFORMATION FOR SEQ ID NO:2:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Met Ala Gly Gln Ser Gln His Ile Lys Asn Lys Arg Gln Gln Phe Asn
 1               5                   10                  15

Ser Gly Arg Glu Leu Ile Asn Ala Val Lys Thr Arg Arg Glu Glu Ala
            20                  25                  30

Gln Ala Phe Lys Ala Leu Ala Glu Asp Val Glu Asn Glu Ile Ser Glu
        35                  40                  45

Glu Ile Asp Gln Tyr Asp Pro Glu Leu Ile Asp Gly Val Arg Val Arg
    50                  55                  60

Trp Ile Ser Gln Gly Val Ala Ala Arg Asp Glu Thr Ala Phe Ser His
65                  70                  75                  80
```

| | | | | | | | | | | | | | | |
|---|---|---|---|---|---|---|---|---|---|---|---|---|---|---|
|Ala|Leu|Lys|Ile|Gly|His|Arg|Leu|Arg|Lys|Ala|Gly|Gln|Arg|Leu|Thr|
| | | |  |85| | | |  |90| | | |  |95| |
|Asp|Ala|Ala|Val|Ile|Asp|Ala|Tyr|Glu|His|Ala|Tyr|Asn|Val|Ala|Gln|
| | | |100| | | |105| | | |110| | |
|Gln|Gln|Gly|Ser|Ala|Gly|Arg|Asp|Ser|Glu|Met|Pro|Pro|Met|Arg|Asp|
| | |115| | | |120| | | |125| | | |
|His|Gln|Thr|Met|Ala|Arg|Arg|Val|Arg|Gly|Tyr|Val|Thr|Gln|Ser|Lys|
| |130| | | |135| | | |140| | | |
|Thr|Asn|Thr|Ser|Leu|Gly|Ala|Ser|Ala|Pro|Gly|Arg|Val|Thr|Ser|Ser|
|145| | | |150| | | |155| | | |160|
|Glu|Arg|Lys|Ala|Leu|Ala|Thr|Met|Gly|Arg|Lys|Gly|Gly|Gln|Lys|Ala|
| | | |165| | | |170| | | |175| |
|Ala|Gln|Arg|Trp|Lys|Thr|Asp|Pro|Glu|Gly|Gln|Tyr|Ala|Gln|Asn|Gln|
| | |180| | | |185| | | |190| | |
|Leu|Gln|Lys|Leu|Lys|Lys|Thr|His|Arg|Lys|Lys|Arg|Val|Glu|Gly|Gln|
| |195| | | |200| | | |205| | | |
|Thr|Thr|Arg|Ala|Lys|Ile|Gln|Ala|Leu|Ile|Gly|Glu|Ala|Tyr|Val|Gln|
| |210| | | |215| | | |220| | | |
|Thr|Gly|Glu|Val|Leu|Thr|Arg|Lys|Gln|Ile|Val|Asp|Glu|Thr|Gly|Leu|
|225| | | |230| | | |235| | | |240|
|Ser|Arg|Ala|Thr|Val|Thr|Arg|His|Leu|Ala|Ala|Leu|Arg|Glu|Gln|Gly|
| | | |245| | | |250| | | |255| |
|Ala|Leu|Pro|Glu|Thr|
| | |260| | |

( 2 ) INFORMATION FOR SEQ ID NO:3:

( i ) SEQUENCE CHARACTERISTICS:
        ( A ) LENGTH: 1897 base pairs
        ( B ) TYPE: nucleic acid
        ( C ) STRANDEDNESS: double
        ( D ) TOPOLOGY: linear ( i i ) MOLECULE TYPE: plasmid DNA ( v i ) ORIGINAL SOURCE:
        ( A ) ORGANISM: Brevibacterium flavum
        ( B ) STRAIN: MJ233 COP2-1.8

( i x ) FEATURE:
        ( A ) NAME/KEY: peptide
        ( B ) LOCATION: 922..1704
        ( C ) IDENTIFICATION METHOD: experiment ( x i ) SEQUENCE DESCRIPTION: SEQ ID NO:3:

```
GCGCAGCCTG ACCATGGACA TGCTTCTACG TTCTTCCACA CTGGTATCTT TTGGTTGCAA      60
TATATATTGC AACCATGCTG GTAAAACAAC TTTTTAGCGT GTCTTGCCCA AAATTACAGT     120
CATGTGATTT ACAGTTGAAA GATACTGAAA ATCAAGAAG GCCACTCGGC GGCAACCGAA      180
TGACCTTCGC TTATCACCCA GTCCTACCTG GGAGAAAGCA TGTACATGAT TATACCCAAT     240
AGTACGCCCG CGTACCCCAT TTCCGGTTCG CGTGTTAACA CGCCATCACG TTTGCGCCCT     300
GACTGCGCAG GCCTTGATGA CACCCCAGCG AGCACCGTTG ACCGGGACAA GCTGCTCGCA     360
CATCTTGGCC GTACAGCACT GCACGGGTCT ATAAGTCGAA ACTTCAAAGG CGCTTATCGC     420
CTCGTTGTGG ATAAGGAAAC GGGGGAAAAG CGAAGCGTTC CGAACCTTTA CCGCATTGAT     480
TCCGAAAAAC TCGGTCGCTG CGAATACGTC ATGCTGACTA GTAAGCAATA TGCTTCGGTC     540
ATGGTCATAG ACGTTGACCA GATAGGAGAG GCTGGAGGAC ATCCAGAAAA CCTCAACTCC     600
TATGTCAAAG GCGTTATCTG GGTACTTGTG CAGCACGGAA TTGGACCAGC ATGGGCAGGC     660
```

| | |
|---|---|
| ATTAATCCGA TTAGTGGTAA AGCGCAGTTT ATTTGGCTTA TTGACCCAGT TTATGCAGGA | 720 |
| AAGAATCGTG CGTCCCGGAA TATGGAGCTA CTCAAAGCCA CAAGTCACGA GTTGGGTGAG | 780 |
| TTACTGGATC ATGATCCACA TTTTGCGCAT CGGTTTAGCC GGAGTCCTTT TTATACTGGA | 840 |
| AAGTCACCGG AGGCTTATCG CTGGTATTGC CAGCATGACC GGGTTATACG CCTCCAAGAC | 900 |
| TTTCTAAGGC AGGTGCGCGA G ATG GCG GGA CAA TCC CAG CAC ATT AAA AAC | 951 |

```
                          Met Ala Gly Gln Ser Gln His Ile Lys Asn
                           1           5                      10

AAG CGC CAG CAA TTT AAC AGT GGC CGT GAG CTT ATT AAT GCG GTC AAA            999
Lys Arg Gln Gln Phe Asn Ser Gly Arg Glu Leu Ile Asn Ala Val Lys
             15                  20                      25

ACT CGC CGT GAA GAA GCC CAA GCC TTT AAA GCA CTT GCT GAG GAT GTC           1047
Thr Arg Arg Glu Glu Ala Gln Ala Phe Lys Ala Leu Ala Glu Asp Val
         30                  35                      40

GAA AAC GAG ATA AGT GAA GAA ATC GAT CAA TAC GAC CCG GAA CTA ATC           1095
Glu Asn Glu Ile Ser Glu Glu Ile Asp Gln Tyr Asp Pro Glu Leu Ile
             45                  50                      55

GAC GGG GTG CGC GTG CGC TGG ATT AGC CAA GGG GTC GCA GCA CGC GAC           1143
Asp Gly Val Arg Val Arg Trp Ile Ser Gln Gly Val Ala Ala Arg Asp
         60                  65                      70

GAA ACA GCG TTT AGC CAC GCA CTA AAA ATT GGT CAC CGC CTA CGC AAA           1191
Glu Thr Ala Phe Ser His Ala Leu Lys Ile Gly His Arg Leu Arg Lys
75                   80                  85                      90

GCA GGA CAA CGA CTC ACA GAC GCC GCC GTT ATC GAT GCC TAC GAG CAT           1239
Ala Gly Gln Arg Leu Thr Asp Ala Ala Val Ile Asp Ala Tyr Glu His
             95                  100                     105

GCC TAT AAC GTT GCA CAA CAA CAA GGC TCA GCA GGC CGA GAC AGC GAA           1287
Ala Tyr Asn Val Ala Gln Gln Gln Gly Ser Ala Gly Arg Asp Ser Glu
         110                 115                     120

ATG CCA CCC ATG CGT GAC CGC CAG ACC ATG GCA CGA CGC GTA CGC GGC           1335
Met Pro Pro Met Arg Asp Arg Gln Thr Met Ala Arg Arg Val Arg Gly
             125                 130                     135

TAT GTC ACC CAA TCC AAA ACC AAC ACA AGT CTA GGA GCT AGC GCT CCC           1383
Tyr Val Thr Gln Ser Lys Thr Asn Thr Ser Leu Gly Ala Ser Ala Pro
         140                 145                     150

GGA CGC GTT ACC AGC AGC GAA CGC AAA GCA CTG GCC ACC ATG GGG CGA           1431
Gly Arg Val Thr Ser Ser Glu Arg Lys Ala Leu Ala Thr Met Gly Arg
155                  160                 165                     170

AAA GGC GGA CAG AAA GCA GCA CAA CGC TGG AAA ACC GAT CCA GAA GGT           1479
Lys Gly Gly Gln Lys Ala Ala Gln Arg Trp Lys Thr Asp Pro Glu Gly
             175                 180                     185

CAA TAC GCA CAA AAT CAG CTG CAG AAA CTA AAG AAA ACG CAC CGG AAG           1527
Gln Tyr Ala Gln Asn Gln Leu Gln Lys Leu Lys Lys Thr His Arg Lys
         190                 195                     200

AAG CGG GTG GAA GGA CAG ACC ACG CGT GCG AAG ATT CAA GCC TTA ATT           1575
Lys Arg Val Glu Gly Gln Thr Thr Arg Ala Lys Ile Gln Ala Leu Ile
             205                 210                     215

GAT GAA GCT TAC GTG CAA ACA GGC GAG GTA CTT ACC CGC AAA CAG ATT           1623
Asp Glu Ala Tyr Val Gln Thr Gly Glu Val Leu Thr Arg Lys Gln Ile
         220                 225                     230

GTG GAT GAG ACA GGA CTA TCT AGA GCT ACA GTG ACA CGG CAT TTG GCG           1671
Val Asp Glu Thr Gly Leu Ser Arg Ala Thr Val Thr Arg His Leu Ala
235              240                 245                     250

GCA CTT CGA GAA CAG GGA GCA CTT CCG GAA ACG TAGGGGCTCA TACCGTAAGC         1724
Ala Leu Arg Glu Gln Gly Ala Leu Pro Glu Thr
             255                 260
```

| | |
|---|---|
| AATATACGGT TCCCCTGCCG GTAGGAATGT AGTAATAACC TCTCTTGAAG AAAACCTTGT | 1784 |
| AGGGCAAGGC TACTTATGCT TCCGGGGTTA GTCGTTCTTC TATTGCGGTG ATGAGTTCTA | 1844 |

GACCTTTATC TAAGTCCTGG GGGCTGCTGT TGCCGTGCGA GGCTTTGCTG CGC    1897

( 2 ) INFORMATION FOR SEQ ID NO:4:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Met Ala Gly Gln Ser Gln His Ile Lys Asn Lys Arg Gln Gln Phe Asn
 1               5                  10                      15

Ser Gly Arg Glu Leu Ile Asn Ala Val Lys Thr Arg Arg Glu Glu Ala
            20                  25                  30

Gln Ala Phe Lys Ala Leu Ala Glu Asp Val Glu Asn Glu Ile Ser Glu
        35                  40                  45

Glu Ile Asp Gln Tyr Asp Pro Glu Leu Ile Asp Gly Val Arg Val Arg
    50                  55                  60

Trp Ile Ser Gln Gly Val Ala Ala Arg Asp Glu Thr Ala Phe Ser His
65                  70                  75                  80

Ala Leu Lys Ile Gly His Arg Leu Arg Lys Ala Gly Gln Arg Leu Thr
                    85                  90                  95

Asp Ala Ala Val Ile Asp Ala Tyr Glu His Ala Tyr Asn Val Ala Gln
                100                 105                 110

Gln Gln Gly Ser Ala Gly Arg Asp Ser Glu Met Pro Pro Met Arg Asp
            115                 120                 125

Arg Gln Thr Met Ala Arg Arg Val Arg Gly Tyr Val Thr Gln Ser Lys
    130                 135                 140

Thr Asn Thr Ser Leu Gly Ala Ser Ala Pro Gly Arg Val Thr Ser Ser
145                 150                 155                 160

Glu Arg Lys Ala Leu Ala Thr Met Gly Arg Lys Gly Gly Gln Lys Ala
                165                 170                 175

Ala Gln Arg Trp Lys Thr Asp Pro Glu Gly Gln Tyr Ala Gln Asn Gln
            180                 185                 190

Leu Gln Lys Leu Lys Lys Thr His Arg Lys Lys Arg Val Glu Gly Gln
        195                 200                 205

Thr Thr Arg Ala Lys Ile Gln Ala Leu Ile Asp Glu Ala Tyr Val Gln
    210                 215                 220

Thr Gly Glu Val Leu Thr Arg Lys Gln Ile Val Asp Glu Thr Gly Leu
225                 230                 235                 240

Ser Arg Ala Thr Val Thr Arg His Leu Ala Ala Leu Arg Glu Gln Gly
                245                 250                 255

Ala Leu Pro Glu Thr
                260
```

( 2 ) INFORMATION FOR SEQ ID NO:5:

( i ) SEQUENCE CHARACTERISTICS:
        ( A ) LENGTH: 1897 base pairs
        ( B ) TYPE: nucleic acid
        ( C ) STRANDEDNESS: double
        ( D ) TOPOLOGY: linear ( i i ) MOLECULE TYPE: plasmid DNA ( v i ) ORIGINAL SOURCE:
        ( A ) ORGANISM: Brevibacterium flavum
        ( B ) STRAIN: MJ233 GE102

-continued ( i x ) FEATURE:
  ( A ) NAME/KEY: peptide
  ( B ) LOCATION: 922..1704
  ( C ) IDENTIFICATION METHOD: experiment ( x i ) SEQUENCE DESCRIPTION: SEQ ID NO:5:

| | | | | | |
|---|---|---|---|---|---|
| GCGCAGCCTG | ACCATGGACA | TGCTTCTACG | TTCTTCCACA | CTGGTATCTT | TTGGTTGCAA | 60 |
| TATATATTGC | AACCATGCTG | GTAAAACAAC | TTTTTAGCGT | GTCTTGCCCA | AAATTACAGT | 120 |
| CATGTGATTT | ACAGTTGAAA | GATACTGAAA | ATCAAAGAAG | GCCACTCGGC | GGCAACCGAA | 180 |
| TGACCTTCGC | TTATCACCCA | GTCCTACCTG | GGAGAAAGCA | TGTACATGAT | TATACCCAAT | 240 |
| AGTACGCCCG | CGTACCCCAT | TTCCGGTTCG | CGTGTTAACA | CGCCATCACG | TTTGCGCCCT | 300 |
| GACTGCGCAG | GCCTTGATGA | CACCCCAGCG | AGCACCGTTG | ACCGGGACAA | GCTGCTCGCA | 360 |
| CATCTTGGCC | GTACAGCACT | GCACGGGTCT | ATAAGTCGAA | ACTTCAAAGG | CGCTTATCGC | 420 |
| CTCGTTGTGG | ATAAGGAAAC | GGGGGAAAAG | CGAAGCGTTC | CGAACCTTTA | CCGCATTGAT | 480 |
| TCCGAAAAAC | TCGGTCGCTG | CGAATACGTC | ATGCTGACTA | GTAAGCAATA | TGCTTCGGTC | 540 |
| ATGGTCATAG | ACGTTGACCA | GATAGGAGAG | GCTGGAGGAC | ATCCAGAAAA | CCTCAACTCC | 600 |
| TATGTCAAAG | GCGTTATCTG | GGTACTTGTG | CAGCACGGAA | TTGGACCAGC | ATGGGCAGGC | 660 |
| ATTAATCCGA | TTAGTGGTAA | AGCGCAGTTT | ATTTGGCTTA | TTGACCCAGT | TTATGCAGGA | 720 |
| AAGAATCGTG | CGTCCCGGAA | TATGGAGCTA | CTCAAAGCCA | CAAGTCACGA | GTTGGGTGAG | 780 |
| TTACTGGATC | ATGATCCACA | TTTTGCGCAT | CGGTTTAGCC | GGAGTCCTTT | TTATACTGGA | 840 |
| AAGTCACCGG | AGGCTTATCG | CTGGTATTGC | CAGCATGACC | GGGTTATACG | CCTCCAAGAC | 900 |
| TTTCTAAGGC | AGGTGCGCGA | G | | | | 921 |

| | | | | | | | | | | |
|---|---|---|---|---|---|---|---|---|---|---|
| | | ATG | GCG | GGA | CAA | TCC | CAG | CAC | ATT | AAA | AAC | 951 |
| | | Met | Ala | Gly | Gln | Ser | Gln | His | Ile | Lys | Asn |
| | | 1 | | | 5 | | | | | | 10 |

| AAG | CGC | CAG | CAA | TTT | AAC | AGT | GGC | CGT | GAG | CTT | ATT | AAT | GCG | GTC | AAA | 999 |
|---|---|---|---|---|---|---|---|---|---|---|---|---|---|---|---|---|
| Lys | Arg | Gln | Gln | Phe | Asn | Ser | Gly | Arg | Glu | Leu | Ile | Asn | Ala | Val | Lys |
| | | | | 15 | | | | 20 | | | | | 25 | | |

| ACT | CGC | CGT | GAA | GAA | GCC | CAA | GCC | TTT | AAA | GCA | CTT | GCT | GAG | GAT | GTC | 1047 |
|---|---|---|---|---|---|---|---|---|---|---|---|---|---|---|---|---|
| Thr | Arg | Arg | Glu | Glu | Ala | Gln | Ala | Phe | Lys | Ala | Leu | Ala | Glu | Asp | Val |
| | | | 30 | | | | 35 | | | | | 40 | | | |

| GAA | AAC | GAG | ATA | AGT | GAA | GAA | ATC | GAT | CAA | TAC | GAC | CCG | GAA | CTA | ATC | 1095 |
|---|---|---|---|---|---|---|---|---|---|---|---|---|---|---|---|---|
| Glu | Asn | Glu | Ile | Ser | Glu | Glu | Ile | Asp | Gln | Tyr | Asp | Pro | Glu | Leu | Ile |
| | | 45 | | | | 50 | | | | | 55 | | | | |

| GAC | GGG | GTG | CGC | GTG | CGC | TGG | ATT | AGC | CAA | GGG | GTC | GCA | GCA | CGC | GAC | 1143 |
|---|---|---|---|---|---|---|---|---|---|---|---|---|---|---|---|---|
| Asp | Gly | Val | Arg | Val | Arg | Trp | Ile | Ser | Gln | Gly | Val | Ala | Ala | Arg | Asp |
| | 60 | | | | 65 | | | | | 70 | | | | | |

| GAA | ACA | GCG | TTT | AGC | CAC | GCA | CTA | AAA | ATT | GGT | CAC | CGC | CTA | CGC | AAA | 1191 |
|---|---|---|---|---|---|---|---|---|---|---|---|---|---|---|---|---|
| Glu | Thr | Ala | Phe | Ser | His | Ala | Leu | Lys | Ile | Gly | His | Arg | Leu | Arg | Lys |
| 75 | | | | | 80 | | | | | 85 | | | | | 90 |

| GCA | GGA | CAA | CGA | CTC | ACA | GAC | GCC | GCC | GTT | ATC | GAT | GCC | TAC | GAG | CAT | 1239 |
|---|---|---|---|---|---|---|---|---|---|---|---|---|---|---|---|---|
| Ala | Gly | Gln | Arg | Leu | Thr | Asp | Ala | Ala | Val | Ile | Asp | Ala | Tyr | Glu | His |
| | | | | 95 | | | | 100 | | | | | 105 | | |

| GCC | TAT | AAC | GTT | GCA | CAA | CAA | CAA | GGC | TCA | GCA | GGC | CGA | GAC | AGC | GAA | 1287 |
|---|---|---|---|---|---|---|---|---|---|---|---|---|---|---|---|---|
| Ala | Tyr | Asn | Val | Ala | Gln | Gln | Gln | Gly | Ser | Ala | Gly | Arg | Asp | Ser | Glu |
| | | | 110 | | | | 115 | | | | | 120 | | | |

| ATG | CCA | CCC | ATG | CGT | GAC | CGC | CAG | ACC | ATG | GCA | CGA | CGC | GTA | CGC | GGC | 1335 |
|---|---|---|---|---|---|---|---|---|---|---|---|---|---|---|---|---|
| Met | Pro | Pro | Met | Arg | Asp | Arg | Gln | Thr | Met | Ala | Arg | Arg | Val | Arg | Gly |
| | | 125 | | | | 130 | | | | | 135 | | | | |

| TAT | GTC | ACC | CAA | TCC | AAA | ACC | AAC | ACA | AGT | CTA | GGA | GCT | AGC | GCT | CCC | 1383 |
|---|---|---|---|---|---|---|---|---|---|---|---|---|---|---|---|---|
| Tyr | Val | Thr | Gln | Ser | Lys | Thr | Asn | Thr | Ser | Leu | Gly | Ala | Ser | Ala | Pro |
| | | 140 | | | | 145 | | | | | 150 | | | | |

| GGA | CGC | GTT | ACC | AGC | AGC | GAA | CGC | AAA | GCA | CTG | GCC | ACC | ATG | GGG | CGA | 1431 |
|---|---|---|---|---|---|---|---|---|---|---|---|---|---|---|---|---|
| Gly | Arg | Val | Thr | Ser | Ser | Glu | Arg | Lys | Ala | Leu | Ala | Thr | Met | Gly | Arg |
| 155 | | | | | 160 | | | | | 165 | | | | | 170 |

| | | | | | | | | | | | | | | | | |
|---|---|---|---|---|---|---|---|---|---|---|---|---|---|---|---|---|
| AAA | GGC | GGA | CAG | AAA | GCA | GCA | CAA | CGC | TGG | AAA | ACC | GAT | CCA | GAA | GGT | 1479 |
| Lys | Gly | Gly | Gln | Lys | Ala | Ala | Gln | Arg | Trp | Lys | Thr | Asp | Pro | Glu | Gly | |
| | | | | 175 | | | | | 180 | | | | | 185 | | |
| CAA | TAC | GCA | CAA | AAT | CAG | CTG | CAG | AAA | CTA | AAG | AAA | ACG | CAC | CGG | AAG | 1527 |
| Gln | Tyr | Ala | Gln | Asn | Gln | Leu | Gln | Lys | Leu | Lys | Lys | Thr | His | Arg | Lys | |
| | | | | 190 | | | | | 195 | | | | | 200 | | |
| AAG | CGG | GTG | GAA | GGA | CAG | ACC | ACG | CGT | GCG | AAG | ATT | CAA | GCC | TTA | ATT | 1575 |
| Lys | Arg | Val | Glu | Gly | Gln | Thr | Thr | Arg | Ala | Lys | Ile | Gln | Ala | Leu | Ile | |
| | | | 205 | | | | 210 | | | | | 215 | | | | |
| GGT | GAA | GCT | TAC | GTG | CAA | ACA | GGC | GAG | GTA | CTT | ACC | CGC | AAA | CAG | ATT | 1623 |
| Gly | Glu | Ala | Tyr | Val | Gln | Thr | Gly | Glu | Val | Leu | Thr | Arg | Lys | Gln | Ile | |
| | 220 | | | | | 225 | | | | | 230 | | | | | |
| GTG | GAT | GAG | ACA | GGA | CTA | TCT | AGA | GCT | ACA | GTG | ACA | CGG | CAT | TTG | GCG | 1671 |
| Val | Asp | Glu | Thr | Gly | Leu | Ser | Arg | Ala | Thr | Val | Thr | Arg | His | Leu | Ala | |
| 235 | | | | | 240 | | | | | 245 | | | | | 250 | |
| GCA | CTT | CGA | GAA | CAG | GGA | GCA | CTT | CCG | GAA | ACG | TAGGGGCTCA | | | TACCGTAAGC | | 1724 |
| Ala | Leu | Arg | Glu | Gln | Gly | Ala | Leu | Pro | Glu | Thr | | | | | | |
| | | | | 255 | | | | | 260 | | | | | | | |

AATATACGGT TCCCCTGCCG GTAGGAATGT AGTAATAACC TCTCTTGAAG AAAACCTTGT 1784

AGGGCAAGGC TACTTATGCT TCCGGGGTTA GTCGTTCTTC TATTGCGGTG ATGAGTTCTA 1844

GACCTTTATC TAAGTCCTGG GGGCTGCTGT TGCCGTGCGA GGCTTTGCTG CGC 1897

( 2 ) INFORMATION FOR SEQ ID NO:6:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

| | | | | | | | | | | | | | | |
|---|---|---|---|---|---|---|---|---|---|---|---|---|---|---|
| Met | Ala | Gly | Gln | Ser | Gln | His | Ile | Lys | Asn | Lys | Arg | Gln | Gln | Phe | Asn |
| 1 | | | | 5 | | | | | 10 | | | | | 15 | |
| Ser | Gly | Arg | Glu | Leu | Ile | Asn | Ala | Val | Lys | Thr | Arg | Arg | Glu | Glu | Ala |
| | | | 20 | | | | | 25 | | | | | 30 | | |
| Gln | Ala | Phe | Lys | Ala | Leu | Ala | Glu | Asp | Val | Glu | Asn | Glu | Ile | Ser | Glu |
| | | | 35 | | | | 40 | | | | | 45 | | | |
| Glu | Ile | Asp | Gln | Tyr | Asp | Pro | Glu | Leu | Ile | Asp | Gly | Val | Arg | Val | Arg |
| | 50 | | | | | 55 | | | | | 60 | | | | |
| Trp | Ile | Ser | Gln | Gly | Val | Ala | Ala | Arg | Asp | Glu | Thr | Ala | Phe | Ser | His |
| 65 | | | | | 70 | | | | 75 | | | | | 80 | |
| Ala | Leu | Lys | Ile | Gly | His | Arg | Leu | Arg | Lys | Ala | Gly | Gln | Arg | Leu | Thr |
| | | | | 85 | | | | | 90 | | | | | 95 | |
| Asp | Ala | Ala | Val | Ile | Asp | Ala | Tyr | Glu | His | Ala | Tyr | Asn | Val | Ala | Gln |
| | | | 100 | | | | | 105 | | | | | 110 | | |
| Gln | Gln | Gly | Ser | Ala | Gly | Arg | Asp | Ser | Glu | Met | Pro | Pro | Met | Arg | Asp |
| | | | 115 | | | | | 120 | | | | 125 | | | |
| Arg | Gln | Thr | Met | Ala | Arg | Arg | Val | Arg | Gly | Tyr | Val | Thr | Gln | Ser | Lys |
| | 130 | | | | | 135 | | | | | 140 | | | | |
| Thr | Asn | Thr | Ser | Leu | Gly | Ala | Ser | Ala | Pro | Gly | Arg | Val | Thr | Ser | Ser |
| 145 | | | | | 150 | | | | | 155 | | | | | 160 |
| Glu | Arg | Lys | Ala | Leu | Ala | Thr | Met | Gly | Arg | Lys | Gly | Gly | Gln | Lys | Ala |
| | | | | 165 | | | | | 170 | | | | | 175 | |
| Ala | Gln | Arg | Trp | Lys | Thr | Asp | Pro | Glu | Gly | Gln | Tyr | Ala | Gln | Asn | Gln |
| | | | 180 | | | | | 185 | | | | | 190 | | |
| Leu | Gln | Lys | Leu | Lys | Lys | Thr | His | Arg | Lys | Lys | Arg | Val | Glu | Gly | Gln |

|     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- |
| Thr | Thr | Arg | Ala | Lys | Ile | Gln | Ala | Leu | Ile | Gly | Glu | Ala | Tyr | Val | Gln |
|     | 210 |     |     |     |     | 215 |     |     |     |     | 220 |     |     |     |     |
| Thr | Gly | Glu | Val | Leu | Thr | Arg | Lys | Gln | Ile | Val | Asp | Glu | Thr | Gly | Leu |
| 225 |     |     |     |     | 230 |     |     |     |     | 235 |     |     |     |     | 240 |
| Ser | Arg | Ala | Thr | Val | Thr | Arg | His | Leu | Ala | Ala | Leu | Arg | Glu | Gln | Gly |
|     |     |     |     | 245 |     |     |     |     | 250 |     |     |     |     | 255 |     |
| Ala | Leu | Pro | Glu | Thr |
|     |     |     | 260 |     |

( 2 ) INFORMATION FOR SEQ ID NO:7:

( i ) SEQUENCE CHARACTERISTICS:
        ( A ) LENGTH: 1897 base pairs
        ( B ) TYPE: nucleic acid
        ( C ) STRANDEDNESS: double
        ( D ) TOPOLOGY: linear ( i i ) MOLECULE TYPE: plasmid DNA ( i i i ) HYPOTHETICAL: YES ( i x ) FEATURE:
        ( A ) NAME/KEY: peptide
        ( B ) LOCATION: 922..1704
        ( C ) IDENTIFICATION METHOD: similarity with known sequence ( x i ) SEQUENCE DESCRIPTION: SEQ ID NO:7:

| | | | | | |
|---|---|---|---|---|---|
| GCGCAGCCTG | ACCATGGACA | TGCTTCTACG | TTCTTCCACA | CTGGTATCTT | TTGGTTGCAA | 60 |
| TATATATTGC | AACCATGCTG | GTAAAACAAC | TTTTTAGCGT | GTCTTGCCCA | AAATTACAGT | 120 |
| CATGTGATTT | ACAGTTGAAA | GATACTGAAA | ATCAAAGAAG | GCCACTCGGC | GGCAACCGAA | 180 |
| TGACCTTCGC | TTATCACCCA | GTCCTACCTG | GGAGAAAGCA | TGTACATGAT | TATACCCAAT | 240 |
| AGTACGCCCG | CGTACCCCAT | TTCCGGTTCG | CGTGTTAACA | CGCCATCACG | TTTGCGCCCT | 300 |
| GACTGCGCAG | GCCTTGATGA | CACCCCAGCG | AGCACCGTTG | ACCGGGACAA | GCTGCTCGCA | 360 |
| CATCTTGGCC | GTACAGCACT | GCACGGGTCT | ATAAGTCGAA | ACTTCAAAGG | CGCTTATCGC | 420 |
| CTCGTTGTGG | ATAAGGAAAC | GGGGGAAAAG | CGAAGCGTTC | CGAACCTTTA | CCGCATTGAT | 480 |
| TCCGAAAAAC | TCGGTCGCTG | CGAATACGTC | ATGCTGACTA | GTAAGCAATA | TGCTTCGGTC | 540 |
| ATGGTCATAG | ACGTTGACCA | GATAGGAGAG | GCTGGAGGAC | ATCCAGAAAA | CCTCAACTCC | 600 |
| TATGTCAAAG | GCGTTATCTG | GGTACTTGTG | CAGCACGGAA | TTGGACCAGC | ATGGGCAGGC | 660 |
| ATTAATCCGA | TTAGTGGTAA | AGCGCAGTTT | ATTTGGCTTA | TTGACCCAGT | TTATGCAGGA | 720 |
| AAGAATCGTG | CGTCCCGGAA | TATGGAGCTA | CTCAAAGCCA | CAAGTCACGA | GTTGGGTGAG | 780 |
| TTACTGGATC | ATGATCCACA | TTTTGCGCAT | CGGTTTAGCC | GGAGTCCTTT | TTATACTGGA | 840 |
| AAGTCACCGG | AGGCTTATCG | CTGGTATTGC | CAGCATGACC | GGGTTATACG | CCTCCAAGAC | 900 |
| TTTCTAAGGC | AGGTGCGCGA | G ATG GCG GGA CAA TCC CAG CAC ATT AAA AAC | | | | 951 |
| | |     Met Ala Gly Gln Ser Gln His Ile Lys Asn | | | |
| | |       1              5             10 | | | |
| AAG CGC CAG CAA TTT AAC AGT GGC CGT GAG CTT ATT AAT GCG GTC AAA | | | | | | 999 |
| Lys Arg Gln Gln Phe Asn Ser Gly Arg Glu Leu Ile Asn Ala Val Lys | | | | | | |
|                15                  20               25 | | | | | | |
| ACT CGC CGT GAA GAA GCC CAA GCC TTT AAA GCA CTT GCT GAG GAT GTC | | | | | | 1047 |
| Thr Arg Arg Glu Glu Ala Gln Ala Phe Lys Ala Leu Ala Glu Asp Val | | | | | | |
|          30                       35               40 | | | | | | |
| GAA AAC GAG ATA AGT GAA GAA ATC GAT CAA TAC GAC CCG GAA CTA ATC | | | | | | 1095 |
| Glu Asn Glu Ile Ser Glu Glu Ile Asp Gln Tyr Asp Pro Glu Leu Ile | | | | | | |
|              45                    50               55 | | | | | | |

| | | | | | | | | | | | | | | | |
|---|---|---|---|---|---|---|---|---|---|---|---|---|---|---|---|
| GAC | GGG | GTG | CGC | GTG | CGC | TGG | ATT | AGC | CAA | GGG | GTC | GCA | GCA | CGC | GAC | 1143
| Asp | Gly | Val | Arg | Val | Arg | Trp | Ile | Ser | Gln | Gly | Val | Ala | Ala | Arg | Asp |
| | 60 | | | | | 65 | | | | | 70 | | | | |
| GAA | ACA | GCG | TTT | AGC | CAC | GCA | CTA | AAA | ATT | GGT | CAC | CGC | CTA | CGC | AAA | 1191
| Glu | Thr | Ala | Phe | Ser | His | Ala | Leu | Lys | Ile | Gly | His | Arg | Leu | Arg | Lys |
| 75 | | | | | 80 | | | | | 85 | | | | | 90 |
| GCA | GGA | CAA | CGA | CTC | ACA | GAC | GCC | GCC | GTT | ATC | GAT | GCC | TAC | GAG | CAT | 1239
| Ala | Gly | Gln | Arg | Leu | Thr | Asp | Ala | Ala | Val | Ile | Asp | Ala | Tyr | Glu | His |
| | | | | 95 | | | | | 100 | | | | | 105 | |
| GCC | TAT | AAC | GTT | GCA | CAA | CAA | CAA | GGC | TCA | GCA | GGC | CGA | GAC | AGC | GAA | 1287
| Ala | Tyr | Asn | Val | Ala | Gln | Gln | Gln | Gly | Ser | Ala | Gly | Arg | Asp | Ser | Glu |
| | | | 110 | | | | | 115 | | | | | 120 | | |
| ATG | CCA | CCC | ATG | CGT | GAC | CGC | CAG | ACC | ATG | GCA | CGA | CGC | GTA | CGC | GGC | 1335
| Met | Pro | Pro | Met | Arg | Asp | Arg | Gln | Thr | Met | Ala | Arg | Arg | Val | Arg | Gly |
| | | 125 | | | | | 130 | | | | | 135 | | | |
| TAT | GTC | ACC | CAA | TCC | AAA | ACC | AAC | ACA | AGT | CTA | GGA | GCT | AGC | GCT | CCC | 1383
| Tyr | Val | Thr | Gln | Ser | Lys | Thr | Asn | Thr | Ser | Leu | Gly | Ala | Ser | Ala | Pro |
| | 140 | | | | | 145 | | | | | 150 | | | | |
| GGA | CGC | GTT | ACC | AGC | AGC | GAA | CGC | AAA | GCA | CTG | GCC | ACC | ATG | GGG | CGA | 1431
| Gly | Arg | Val | Thr | Ser | Ser | Glu | Arg | Lys | Ala | Leu | Ala | Thr | Met | Gly | Arg |
| 155 | | | | | 160 | | | | | 165 | | | | | 170 |
| AAA | GGC | GGA | CAG | AAA | GCA | GCA | CAA | CGC | TGG | AAA | ACC | GAT | CCA | GAA | GGT | 1479
| Lys | Gly | Gly | Gln | Lys | Ala | Ala | Gln | Arg | Trp | Lys | Thr | Asp | Pro | Glu | Gly |
| | | | | 175 | | | | | 180 | | | | | 185 | |
| CAA | TAC | GCA | CAA | AAT | CAG | CTG | CAG | AAA | CTA | AAG | AAA | ACG | CAC | CGG | AAG | 1527
| Gln | Tyr | Ala | Gln | Asn | Gln | Leu | Gln | Lys | Leu | Lys | Lys | Thr | His | Arg | Lys |
| | | | 190 | | | | | 195 | | | | | 200 | | |
| AAG | CGG | GTG | GAA | GGA | CAG | ACC | ACG | CGT | GCG | AAG | ATT | CAA | GCC | TTA | ATT | 1575
| Lys | Arg | Val | Glu | Gly | Gln | Thr | Thr | Arg | Ala | Lys | Ile | Gln | Ala | Leu | Ile |
| | | 205 | | | | | 210 | | | | | 215 | | | |
| GAT | GAA | GCT | TAC | GTG | CAA | ACA | GGC | GAG | GTA | CTT | ACC | CGC | AAA | CAG | ATT | 1623
| Asp | Glu | Ala | Tyr | Val | Gln | Thr | Gly | Glu | Val | Leu | Thr | Arg | Lys | Gln | Ile |
| | 220 | | | | | 225 | | | | | 230 | | | | |
| GTG | GAT | GAG | ACA | GGA | CTA | TCT | AGA | GCT | ACA | GTG | ACA | CGG | CAT | TTG | GCG | 1671
| Val | Asp | Glu | Thr | Gly | Leu | Ser | Arg | Ala | Thr | Val | Thr | Arg | His | Leu | Ala |
| 235 | | | | | 240 | | | | | 245 | | | | | 250 |
| GCA | CTT | CGA | GAA | CAG | GGA | GCA | CTT | CCG | GAA | ACG | TAGGGGCTCA | | TACCGTAAGC | | 1724
| Ala | Leu | Arg | Glu | Gln | Gly | Ala | Leu | Pro | Glu | Thr | | | | | |
| | | | | 255 | | | | | 260 | | | | | | |

AATATACGGT TCCCCTGCCG GTAGGAATGT AGTAATAACC TCTCTTGAAG AAAACCTTGT 1784

AGGGCAAGGC TACTTATGCT TCCGGGGTTA GTCGTTCTTC TATTGCGGTG ATGAGTTCTA 1844

GACCTTTATC TAAGTCCTGG GGGCTGCTGT TGCCGTGCGA GGCTTTGCTG CGC 1897

( 2 ) INFORMATION FOR SEQ ID NO:8:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

| | | | | | | | | | | | | | | |
|---|---|---|---|---|---|---|---|---|---|---|---|---|---|---|
| Met | Ala | Gly | Gln | Ser | Gln | His | Ile | Lys | Asn | Lys | Arg | Gln | Gln | Phe | Asn |
| 1 | | | | 5 | | | | | 10 | | | | | 15 | |
| Ser | Gly | Arg | Glu | Leu | Ile | Asn | Ala | Val | Lys | Thr | Arg | Arg | Glu | Glu | Ala |
| | | | 20 | | | | | 25 | | | | | 30 | | |
| Gln | Ala | Phe | Lys | Ala | Leu | Ala | Glu | Asp | Val | Glu | Asn | Glu | Ile | Ser | Glu |
| | | | | 35 | | | | | 40 | | | | | 45 | |
| Glu | Ile | Asp | Gln | Tyr | Asp | Pro | Glu | Leu | Ile | Asp | Gly | Val | Arg | Val | Arg |

|   | 50 |   |   |   |   | 55 |   |   |   |   | 60 |   |   |   |   |
|---|---|---|---|---|---|---|---|---|---|---|---|---|---|---|---|

Trp Ile Ser Gln Gly Val Ala Ala Arg Asp Glu Thr Ala Phe Ser His
65     70     75     80

Ala Leu Lys Ile Gly His Arg Leu Arg Lys Ala Gly Gln Arg Leu Thr
    85     90     95

Asp Ala Ala Val Ile Asp Ala Tyr Glu His Ala Tyr Asn Val Ala Gln
   100     105     110

Gln Gln Gly Ser Ala Gly Arg Asp Ser Glu Met Pro Pro Met Arg Asp
  115     120     125

Arg Gln Thr Met Ala Arg Arg Val Arg Gly Tyr Val Thr Gln Ser Lys
 130     135     140

Thr Asn Thr Ser Leu Gly Ala Ser Ala Pro Gly Arg Val Thr Ser Ser
145     150     155     160

Glu Arg Lys Ala Leu Ala Thr Met Gly Arg Lys Gly Gly Gln Lys Ala
    165     170     175

Ala Gln Arg Trp Lys Thr Asp Pro Glu Gly Gln Tyr Ala Gln Asn Gln
   180     185     190

Leu Gln Lys Leu Lys Lys Thr His Arg Lys Lys Arg Val Glu Gly Gln
  195     200     205

Thr Thr Arg Ala Lys Ile Gln Ala Leu Ile Asp Glu Ala Tyr Val Gln
 210     215     220

Thr Gly Glu Val Leu Thr Arg Lys Gln Ile Val Asp Glu Thr Gly Leu
225     230     235     240

Ser Arg Ala Thr Val Thr Arg His Leu Ala Ala Leu Arg Glu Gln Gly
    245     250     255

Ala Leu Pro Glu Thr
   260

( 2 ) INFORMATION FOR SEQ ID NO:9:

( i ) SEQUENCE CHARACTERISTICS:
  ( A ) LENGTH: 1897 base pairs
  ( B ) TYPE: nucleic acid
  ( C ) STRANDEDNESS: double
  ( D ) TOPOLOGY: linear ( i i ) MOLECULE TYPE: plasmid DNA ( i i i ) HYPOTHETICAL: YES ( i x ) FEATURE:
  ( A ) NAME/KEY: peptide
  ( B ) LOCATION: 922..1704
  ( C ) IDENTIFICATION METHOD: similarity with known sequence ( x i ) SEQUENCE DESCRIPTION: SEQ ID NO:9:

```
GCGCAGCCTG ACCATGGACA TGCTTCTACG TTCTTCCACA CTGGTATCTT TTGGTTGCAA        60
TATATATTGC AACCATGCTG GTAAAACAAC TTTTTAGCGT GTCTTGCCCA AAATTACAGT       120
CATGTGATTT ACAGTTGAAA GATACTGAAA ATCAAGAAG GCCACTCGGC GGCAACCGAA        180
TGACCTTCGC TTATCACCCA GTCCTACCTG GGAGAAAGCA TGTACATGAT TATACCCAAT       240
AGTACGCCCG CGTACCCCAT TTCCGGTTCG CGTGTTAACA CGCCATCACG TTTGCGCCCT       300
GACTGCGCAG GCCTTGATGA CACCCCAGCG AGCACCGTTG ACCGGGACAA GCTGCTCGCA       360
CATCTTGGCC GTACAGCACT GCACGGGTCT ATAAGTCGAA ACTTCAAAGG CGCTTATCGC       420
CTCGTTGTGG ATAAGGAAAC GGGGGAAAAG CGAAGCGTTC CGAACCTTTA CCGCATTGAT       480
TCCGAAAAAC TCGGTCGCTG CGAATACGTC ATGCTGACTA GTAAGCAATA TGCTTCGGTC       540
ATGGTCATAG ACGTTGACCA GATAGGAGAG GCTGGAGGAC ATCCAGAAAA CCTCAACTCC       600
```

```
TATGTCAAAG GCGTTATCTG GGTACTTGTG CAGCACGGAA TTGGACCAGC ATGGGCAGGC      660

ATTAATCCGA TTAGTGGTAA AGCGCAGTTT ATTTGGCTTA TTGACCCAGT TTATGCAGGA      720

AAGAATCGTG CGTCCCGGAA TATGGAGCTA CTCAAAGCCA CAAGTCACGA GTTGGGTGAG      780

TTACTGGATC ATGATCCACA TTTTGCGCAT CGGTTTAGCC GGAGTCCTTT TTATACTGGA      840

AAGTCACCGG AGGCTTATCG CTGGTATTGC CAGCATGACC GGGTTATACG CCTCCAAGAC      900

TTTCTAAGGC AGGTGCGCGA G ATG GCG GGA CAA TCC CAG CAC ATT AAA AAC       951
                        Met Ala Gly Gln Ser Gln His Ile Lys Asn
                         1                5                    10
```

| | | | | | | | | | | | | | | | | |
|---|---|---|---|---|---|---|---|---|---|---|---|---|---|---|---|---|
| AAG | CGC | CAG | CAA | TTT | AAC | AGT | GGC | CGT | GAG | CTT | ATT | AAT | GCG | GTC | AAA | 999 |
| Lys | Arg | Gln | Gln | Phe | Asn | Ser | Gly | Arg | Glu | Leu | Ile | Asn | Ala | Val | Lys | |
|  |  |  |  | 15 |  |  |  |  | 20 |  |  |  |  | 25 |  |  |
| ACT | CGC | CGT | GAA | GAA | GCC | CAA | GCC | TTT | AAA | GCA | CTT | GCT | GAG | GAT | GTC | 1047 |
| Thr | Arg | Arg | Glu | Glu | Ala | Gln | Ala | Phe | Lys | Ala | Leu | Ala | Glu | Asp | Val | |
|  |  | 30 |  |  |  |  | 35 |  |  |  |  | 40 |  |  |  |  |
| GAA | AAC | GAG | ATA | AGT | GAA | GAA | ATC | GAT | CAA | TAC | GAC | CCG | GAA | CTA | ATC | 1095 |
| Glu | Asn | Glu | Ile | Ser | Glu | Glu | Ile | Asp | Gln | Tyr | Asp | Pro | Glu | Leu | Ile | |
|  |  | 45 |  |  |  | 50 |  |  |  |  | 55 |  |  |  |  |  |
| GAC | GGG | GTG | CGC | GTG | CGC | TGG | ATT | AGC | CAA | GGG | GTC | GCA | GCA | CGC | GAC | 1143 |
| Asp | Gly | Val | Arg | Val | Arg | Trp | Ile | Ser | Gln | Gly | Val | Ala | Ala | Arg | Asp | |
|  | 60 |  |  |  |  | 65 |  |  |  |  | 70 |  |  |  |  |  |
| GAA | ACA | GCG | TTT | AGC | CAC | GCA | CTA | AAA | ATT | GGT | CAC | CGC | CTA | CGC | AAA | 1191 |
| Glu | Thr | Ala | Phe | Ser | His | Ala | Leu | Lys | Ile | Gly | His | Arg | Leu | Arg | Lys | |
| 75 |  |  |  |  | 80 |  |  |  |  | 85 |  |  |  |  | 90 |  |
| GCA | GGA | CAA | CGA | CTC | ACA | GAC | GCC | GCC | GTT | ATC | GAT | GCC | TAC | GAG | CAT | 1239 |
| Ala | Gly | Gln | Arg | Leu | Thr | Asp | Ala | Ala | Val | Ile | Asp | Ala | Tyr | Glu | His | |
|  |  |  |  | 95 |  |  |  |  | 100 |  |  |  |  | 105 |  |  |
| GCC | TAT | AAC | GTT | GCA | CAA | CAA | CAA | GGC | TCA | GCA | GGC | CGA | GAC | AGC | GAA | 1287 |
| Ala | Tyr | Asn | Val | Ala | Gln | Gln | Gln | Gly | Ser | Ala | Gly | Arg | Asp | Ser | Glu | |
|  |  |  | 110 |  |  |  |  | 115 |  |  |  |  | 120 |  |  |  |
| ATG | CCA | CCC | ATG | CGT | GAC | CAC | CAG | ACC | ATG | GCA | CGA | CGC | GTA | CGC | GGC | 1335 |
| Met | Pro | Pro | Met | Arg | Asp | His | Gln | Thr | Met | Ala | Arg | Arg | Val | Arg | Gly | |
|  |  | 125 |  |  |  |  | 130 |  |  |  |  | 135 |  |  |  |  |
| TAT | GTC | ACC | CAA | TCC | AAA | ACC | AAC | ACA | AGT | CTA | GGA | GCT | AGC | GCT | CCC | 1383 |
| Tyr | Val | Thr | Gln | Ser | Lys | Thr | Asn | Thr | Ser | Leu | Gly | Ala | Ser | Ala | Pro | |
|  |  | 140 |  |  |  | 145 |  |  |  |  | 150 |  |  |  |  |  |
| GGA | CGC | GTT | ACC | AGC | AGC | GAA | CGC | AAA | GCA | CTG | GCC | ACC | ATG | GGG | CGA | 1431 |
| Gly | Arg | Val | Thr | Ser | Ser | Glu | Arg | Lys | Ala | Leu | Ala | Thr | Met | Gly | Arg | |
| 155 |  |  |  |  | 160 |  |  |  |  | 165 |  |  |  |  | 170 |  |
| AAA | GGC | GGA | CAG | AAA | GCA | GCA | CAA | CGC | TGG | AAA | ACC | GAT | CCA | GAA | GGT | 1479 |
| Lys | Gly | Gly | Gln | Lys | Ala | Ala | Gln | Arg | Trp | Lys | Thr | Asp | Pro | Glu | Gly | |
|  |  |  |  | 175 |  |  |  |  | 180 |  |  |  |  | 185 |  |  |
| CAA | TAC | GCA | CAA | AAT | CAG | CTG | CAG | AAA | CTA | AAG | AAA | ACG | CAC | CGG | AAG | 1527 |
| Gln | Tyr | Ala | Gln | Asn | Gln | Leu | Gln | Lys | Leu | Lys | Lys | Thr | His | Arg | Lys | |
|  |  |  | 190 |  |  |  |  | 195 |  |  |  |  | 200 |  |  |  |
| AAG | CGG | GTG | GAA | GGA | CAG | ACC | ACG | CGT | GCG | AAG | ATT | CAA | GCC | TTA | ATT | 1575 |
| Lys | Arg | Val | Glu | Gly | Gln | Thr | Thr | Arg | Ala | Lys | Ile | Gln | Ala | Leu | Ile | |
|  |  | 205 |  |  |  |  | 210 |  |  |  |  | 215 |  |  |  |  |
| GAT | GAA | GCT | TAC | GTG | CAA | ACA | GGC | GAG | GTA | CTT | ACC | CGC | AAA | CAG | ATT | 1623 |
| Asp | Glu | Ala | Tyr | Val | Gln | Thr | Gly | Glu | Val | Leu | Thr | Arg | Lys | Gln | Ile | |
|  | 220 |  |  |  |  | 225 |  |  |  |  | 230 |  |  |  |  |  |
| GTG | GAT | GAG | ACA | GGA | CTA | TCT | AGA | GCT | ACA | GTG | ACA | CGG | CAT | TTG | GCG | 1671 |
| Val | Asp | Glu | Thr | Gly | Leu | Ser | Arg | Ala | Thr | Val | Thr | Arg | His | Leu | Ala | |
| 235 |  |  |  |  | 240 |  |  |  |  | 245 |  |  |  |  | 250 |  |
| GCA | CTT | CGA | GAA | CAG | GGA | GCA | CTT | CCG | GAA | ACG | TAGGGGCTCA | | TACCGTAAGC | | | 1724 |
| Ala | Leu | Arg | Glu | Gln | Gly | Ala | Leu | Pro | Glu | Thr | | | | | | |
|  |  |  |  | 255 |  |  |  |  | 260 |  |  |  |  |  |  |  |

```
AATATACGGT TCCCCTGCCG GTAGGAATGT AGTAATAACC TCTCTTGAAG AAAACCTTGT     1784
```

AGGGCAAGGC TACTTATGCT TCCGGGGTTA GTCGTTCTTC TATTGCGGTG ATGAGTTCTA 1844

GACCTTTATC TAAGTCCTGG GGGCTGCTGT TGCCGTGCGA GGCTTTGCTG CGC 1897

( 2 ) INFORMATION FOR SEQ ID NO:10:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

| Met | Ala | Gly | Gln | Ser | Gln | His | Ile | Lys | Asn | Lys | Arg | Gln | Gln | Phe | Asn |
|---|---|---|---|---|---|---|---|---|---|---|---|---|---|---|---|
| 1 | | | | 5 | | | | | 10 | | | | | 15 | |
| Ser | Gly | Arg | Glu | Leu | Ile | Asn | Ala | Val | Lys | Thr | Arg | Arg | Glu | Glu | Ala |
| | | | 20 | | | | | 25 | | | | | 30 | | |
| Gln | Ala | Phe | Lys | Ala | Leu | Ala | Glu | Asp | Val | Glu | Asn | Glu | Ile | Ser | Glu |
| | | | 35 | | | | | 40 | | | | | 45 | | |
| Glu | Ile | Asp | Gln | Tyr | Asp | Pro | Glu | Leu | Ile | Asp | Gly | Val | Arg | Val | Arg |
| | 50 | | | | | 55 | | | | | 60 | | | | |
| Trp | Ile | Ser | Gln | Gly | Val | Ala | Ala | Arg | Asp | Glu | Thr | Ala | Phe | Ser | His |
| 65 | | | | | 70 | | | | | 75 | | | | | 80 |
| Ala | Leu | Lys | Ile | Gly | His | Arg | Leu | Arg | Lys | Ala | Gly | Gln | Arg | Leu | Thr |
| | | | | 85 | | | | | 90 | | | | | 95 | |
| Asp | Ala | Ala | Val | Ile | Asp | Ala | Tyr | Glu | His | Ala | Tyr | Asn | Val | Ala | Gln |
| | | | 100 | | | | | 105 | | | | | 110 | | |
| Gln | Gln | Gly | Ser | Ala | Gly | Arg | Asp | Ser | Glu | Met | Pro | Pro | Met | Arg | Asp |
| | | | 115 | | | | | 120 | | | | | 125 | | |
| His | Gln | Thr | Met | Ala | Arg | Arg | Val | Arg | Gly | Tyr | Val | Thr | Gln | Ser | Lys |
| | 130 | | | | | 135 | | | | | 140 | | | | |
| Thr | Asn | Thr | Ser | Leu | Gly | Ala | Ser | Ala | Pro | Gly | Arg | Val | Thr | Ser | Ser |
| 145 | | | | | 150 | | | | | 155 | | | | | 160 |
| Glu | Arg | Lys | Ala | Leu | Ala | Thr | Met | Gly | Arg | Lys | Gly | Gly | Gln | Lys | Ala |
| | | | | 165 | | | | | 170 | | | | | 175 | |
| Ala | Gln | Arg | Trp | Lys | Thr | Asp | Pro | Glu | Gly | Gln | Tyr | Ala | Gln | Asn | Gln |
| | | | 180 | | | | | 185 | | | | | 190 | | |
| Leu | Gln | Lys | Leu | Lys | Lys | Thr | His | Arg | Lys | Lys | Arg | Val | Glu | Gly | Gln |
| | | | 195 | | | | | 200 | | | | | 205 | | |
| Thr | Thr | Arg | Ala | Lys | Ile | Gln | Ala | Leu | Ile | Asp | Glu | Ala | Tyr | Val | Gln |
| | 210 | | | | | 215 | | | | | 220 | | | | |
| Thr | Gly | Glu | Val | Leu | Thr | Arg | Lys | Gln | Ile | Val | Asp | Glu | Thr | Gly | Leu |
| 225 | | | | | 230 | | | | | 235 | | | | | 240 |
| Ser | Arg | Ala | Thr | Val | Thr | Arg | His | Leu | Ala | Ala | Leu | Arg | Glu | Gln | Gly |
| | | | | 245 | | | | | 250 | | | | | 255 | |
| Ala | Leu | Pro | Glu | Thr |
| | | | | 260 |

( 2 ) INFORMATION FOR SEQ ID NO:11:

( i ) SEQUENCE CHARACTERISTICS:
        ( A ) LENGTH: 1897 base pairs
        ( B ) TYPE: nucleic acid
        ( C ) STRANDEDNESS: double
        ( D ) TOPOLOGY: linear ( i i ) MOLECULE TYPE: plasmid DNA ( i i i ) HYPOTHETICAL: YES

5,597,727

59 60

-continued ( i x ) FEATURE:
  ( A ) NAME/KEY: peptide
  ( B ) LOCATION: 922..1704
  ( C ) IDENTIFICATION METHOD: similarity with known sequence ( x i ) SEQUENCE DESCRIPTION: SEQ ID NO:11:

| | | | | | |
|---|---|---|---|---|---|
| GCGCAGCCTG | ACCATGGACA | TGCTTCTACG | TTCTTCCACA | CTGGTATCTT | TTGGTTGCAA | 60 |
| TATATATTGC | AACCATGCTG | GTAAACAAC | TTTTAGCGT | GTCTTGCCCA | AAATTACAGT | 120 |
| CATGTGATTT | ACAGTTGAAA | GATACTGAAA | ATCAAAGAAG | GCCACTCGGC | GGCAACCGAA | 180 |
| TGACCTTCGC | TTATCACCCA | GTCCTACCTG | GGAGAAAGCA | TGTACATGAT | TATACCCAAT | 240 |
| AGTACGCCCG | CGTACCCCAT | TTCCGGTTCG | CGTGTTAACA | CGCCATCACG | TTTGCGCCCT | 300 |
| GACTGCGCAG | GCCTTGATGA | CACCCCAGCG | AGCACCGTTG | ACCGGGACAA | GCTGCTCGCA | 360 |
| CATCTTGGCC | GTACAGCACT | GCACGGGTCT | ATAAGTCGAA | ACTTCAAAGG | CGCTTATCGC | 420 |
| CTCGTTGTGG | ATAAGGAAAC | GGGGGAAAAG | CGAAGCGTTC | CGAACCTTTA | CCGCATTGAT | 480 |
| TCCGAAAAAC | TCGGTCGCTG | CGAATACGTC | ATGCTGACTA | GTAAGCAATA | TGCTTCGGTC | 540 |
| ATGGTCATAG | ACGTTGACCA | GATAGGAGAG | GCTGGAGGAC | ATCCAGAAAA | CCTCAACTCC | 600 |
| TATGTCAAAG | GCGTTATCTG | GGTACTTGTG | CAGCACGGAA | TTGGACCAGC | ATGGGCAGGC | 660 |
| ATTAATCCGA | TTAGTGGTAA | AGCGCAGTTT | ATTTGGCTTA | TTGACCCAGT | TTATGCAGGA | 720 |
| AAGAATCGTG | CGTCCCGGAA | TATGGAGCTA | CTCAAAGCCA | CAAGTCACGA | GTTGGGTGAG | 780 |
| TTACTGGATC | ATGATCCACA | TTTTGCGCAT | CGGTTTAGCC | GGAGTCCTTT | TTATACTGGA | 840 |
| AAGTCACCGG | AGGCTTATCG | CTGGTATTGC | CAGCATGACC | GGGTTATACG | CCTCCAAGAC | 900 |

| TTTCTAAGGC | AGGTGCGCGA | G | ATG | GCG | GGA | CAA | TCC | CAG | CAC | ATT | AAA | AAC | 951 |
|---|---|---|---|---|---|---|---|---|---|---|---|---|---|
| | | | Met | Ala | Gly | Gln | Ser | Gln | His | Ile | Lys | Asn | |
| | | | 1 | | | | 5 | | | | | 10 | |

| AAG | CGC | CAG | CAA | TTT | AAC | AGT | GGC | CGT | GAG | CTT | ATT | AAT | GCG | GTC | AAA | 999 |
|---|---|---|---|---|---|---|---|---|---|---|---|---|---|---|---|---|
| Lys | Arg | Gln | Gln | Phe | Asn | Ser | Gly | Arg | Glu | Leu | Ile | Asn | Ala | Val | Lys | |
| | | | | 15 | | | | 20 | | | | | 25 | | | |

| ACT | CGC | CGT | GAA | GAA | GCC | CAA | GCC | TTT | AAA | GCA | CTT | GCT | GAG | GAT | GTC | 1047 |
|---|---|---|---|---|---|---|---|---|---|---|---|---|---|---|---|---|
| Thr | Arg | Arg | Glu | Glu | Ala | Gln | Ala | Phe | Lys | Ala | Leu | Ala | Glu | Asp | Val | |
| | | | 30 | | | | 35 | | | | 40 | | | | | |

| GAA | AAC | GAG | ATA | AGT | GAA | GAA | ATC | GAT | CAA | TAC | GAC | CCG | GAA | CTA | ATC | 1095 |
|---|---|---|---|---|---|---|---|---|---|---|---|---|---|---|---|---|
| Glu | Asn | Glu | Ile | Ser | Glu | Glu | Ile | Asp | Gln | Tyr | Asp | Pro | Glu | Leu | Ile | |
| | | 45 | | | | 50 | | | | | 55 | | | | | |

| GAC | GGG | GTG | CGC | GTG | CGC | TGG | ATT | AGC | CAA | GGG | GTC | GCA | GCA | CGC | GAC | 1143 |
|---|---|---|---|---|---|---|---|---|---|---|---|---|---|---|---|---|
| Asp | Gly | Val | Arg | Val | Arg | Trp | Ile | Ser | Gln | Gly | Val | Ala | Ala | Arg | Asp | |
| | 60 | | | | 65 | | | | | 70 | | | | | | |

| GAA | ACA | GCG | TTT | AGC | CAC | GCA | CTA | AAA | ATT | GGT | CAC | CGC | CTA | CGC | AAA | 1191 |
|---|---|---|---|---|---|---|---|---|---|---|---|---|---|---|---|---|
| Glu | Thr | Ala | Phe | Ser | His | Ala | Leu | Lys | Ile | Gly | His | Arg | Leu | Arg | Lys | |
| 75 | | | | 80 | | | | 85 | | | | | 90 | | | |

| GCA | GGA | CAA | CGA | CTC | ACA | GAC | GCC | GCC | GTT | ATC | GAT | GCC | TAC | GAG | CAT | 1239 |
|---|---|---|---|---|---|---|---|---|---|---|---|---|---|---|---|---|
| Ala | Gly | Gln | Arg | Leu | Thr | Asp | Ala | Ala | Val | Ile | Asp | Ala | Tyr | Glu | His | |
| | | | 95 | | | | 100 | | | | | 105 | | | | |

| GCC | TAT | AAC | GTT | GCA | CAA | CAA | CAA | GGC | TCA | GCA | GGC | CGA | GAC | AGC | GAA | 1287 |
|---|---|---|---|---|---|---|---|---|---|---|---|---|---|---|---|---|
| Ala | Tyr | Asn | Val | Ala | Gln | Gln | Gln | Gly | Ser | Ala | Gly | Arg | Asp | Ser | Glu | |
| | | | 110 | | | | 115 | | | | | 120 | | | | |

| ATG | CCA | CCC | ATG | CGT | GAC | CAC | CAG | ACC | ATG | GCA | CGA | CGC | GTA | CGC | GGC | 1335 |
|---|---|---|---|---|---|---|---|---|---|---|---|---|---|---|---|---|
| Met | Pro | Pro | Met | Arg | Asp | His | Gln | Thr | Met | Ala | Arg | Arg | Val | Arg | Gly | |
| | | 125 | | | | 130 | | | | | 135 | | | | | |

| TAT | GTC | ACC | CAA | TCC | AAA | ACC | AAC | ACA | AGT | CTA | GGA | GCT | AGC | GCT | CCC | 1383 |
|---|---|---|---|---|---|---|---|---|---|---|---|---|---|---|---|---|
| Tyr | Val | Thr | Gln | Ser | Lys | Thr | Asn | Thr | Ser | Leu | Gly | Ala | Ser | Ala | Pro | |
| | | 140 | | | | 145 | | | | | 150 | | | | | |

| GGA | CGC | GTT | ACC | AGC | AGC | GAA | CGC | AAA | GCA | CTG | GCC | ACC | ATG | GGG | CGA | 1431 |
|---|---|---|---|---|---|---|---|---|---|---|---|---|---|---|---|---|
| Gly | Arg | Val | Thr | Ser | Ser | Glu | Arg | Lys | Ala | Leu | Ala | Thr | Met | Gly | Arg | |

| | | | | | | | | | | | | | | | | |
|---|---|---|---|---|---|---|---|---|---|---|---|---|---|---|---|---|
|155| | | | |160| | | | |165| | | | |170| |
|AAA|GGC|GGA|CAG|AAA|GCA|GCA|CAA|CGC|TGG|AAA|ACC|GAT|CCA|GAA|GGT|1479|
|Lys|Gly|Gly|Gln|Lys 175|Ala|Ala|Gln|Arg|Trp 180|Lys|Thr|Asp|Pro|Glu 185|Gly| |
|CAA|TAC|GCA|CAA|AAT|CAG|CTG|CAG|AAA|CTA|AAG|AAA|ACG|CAC|CGG|AAG|1527|
|Gln|Tyr|Ala|Gln 190|Asn|Gln|Leu|Gln|Lys 195|Leu|Lys|Lys|Thr|His 200|Arg|Lys| |
|AAG|CGG|GTG|GAA|GGA|CAG|ACC|ACG|CGT|GCG|AAG|ATT|CAA|GCC|TTA|ATT|1575|
|Lys|Arg|Val 205|Glu|Gly|Gln|Thr|Thr 210|Arg|Ala|Lys|Ile|Gln 215|Ala|Leu|Ile| |
|GGT|GAA|GCT|TAC|GTG|CAA|ACA|GGC|GAG|GTA|CTT|ACC|CGC|AAA|CAG|ATT|1623|
|Gly|Glu 220|Ala|Tyr|Val|Gln 225|Thr|Gly|Glu|Val|Leu 230|Thr|Arg|Lys|Gln|Ile| |
|GTG|GAT|GAG|ACA|GGA|CTA|TCT|AGA|GCT|ACA|GTG|ACA|CGG|CAT|TTG|GCG|1671|
|Val 235|Asp|Glu|Thr|Gly|Leu 240|Ser|Arg|Ala|Thr|Val 245|Thr|Arg|His|Leu|Ala 250| |
|GCA|CTT|CGA|GAA|CAG|GGA|GCA|CTT|CCG|GAA|ACG|TAGGGGCTCA|  |TACCGTAAGC|  |  |1724|
|Ala|Leu|Arg|Glu|Gln 255|Gly|Ala|Leu|Pro|Glu 260|Thr| | | | | | |

AATATACGGT TCCCCTGCCG GTAGGAATGT AGTAATAACC TCTCTTGAAG AAAACCTTGT 1784

AGGGCAAGGC TACTTATGCT TCCGGGGTTA GTCGTTCTTC TATTGCGGTG ATGAGTTCTA 1844

GACCTTTATC TAAGTCCTGG GGGCTGCTGT TGCCGTGCGA GGCTTTGCTG CGC 1897

( 2 ) INFORMATION FOR SEQ ID NO:12:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

| | | | | | | | | | | | | | | |
|---|---|---|---|---|---|---|---|---|---|---|---|---|---|---|
|Met 1|Ala|Gly|Gln|Ser 5|Gln|His|Ile|Lys|Asn 10|Lys|Arg|Gln|Gln|Phe 15|
|Asn|Ser|Gly|Arg|Glu 20|Leu|Ile|Asn|Ala|Val 25|Lys|Thr|Arg|Arg|Glu 30|
|Glu|Ala|Gln|Ala|Phe 35|Lys|Ala|Leu|Ala|Glu 40|Asp|Val|Glu|Asn|Glu 45|
|Ile|Ser|Glu|Glu|Ile 50|Asp|Gln|Tyr|Asp|Pro 55|Glu|Leu|Ile|Asp|Gly 60|
|Val|Arg|Val|Arg|Trp 65|Ile|Ser|Gln|Gly|Val 70|Ala|Ala|Arg|Asp|Glu 75|
|Thr|Ala|Phe|Ser|His 80|Ala|Leu|Lys|Ile|Gly 85|His|Arg|Leu|Arg|Lys 90|
|Ala|Gly|Gln|Arg|Leu 95|Thr|Asp|Ala|Ala|Val 100|Ile|Asp|Ala|Tyr|Glu 105|
|His|Ala|Tyr|Asn|Val 110|Ala|Gln|Gln|Gln|Gly 115|Ser|Ala|Gly|Arg|Asp 120|
|Ser|Glu|Met|Pro|Pro 125|Met|Arg|Asp|His|Gln 130|Thr|Met|Ala|Arg|Arg 135|
|Val|Arg|Gly|Tyr|Val 140|Thr|Gln|Ser|Lys|Thr 145|Asn|Thr|Ser|Leu|Gly 150|
|Ala|Ser|Ala|Pro|Gly 155|Arg|Val|Thr|Ser|Ser 160|Glu|Arg|Lys|Ala|Leu 165|
|Ala|Thr|Met|Gly|Arg 170|Lys|Gly|Gly|Gln|Lys 175|Ala|Ala|Gln|Arg|Trp 180|
|Lys|Thr|Asp|Pro|Glu 185|Gly|Gln|Tyr|Ala|Gln 190|Asn|Gln| | | |

|   |   |   |   |   |   |   |   |   |   |   |   |   |   |
|---|---|---|---|---|---|---|---|---|---|---|---|---|---|
| Leu | Gln | Lys 195 | Leu | Lys | Thr | His 200 | Arg | Lys | Lys | Arg 205 | Val | Glu | Gly | Gln |
| Thr | Thr 210 | Arg | Ala | Lys | Ile | Gln 215 | Ala | Leu | Ile | Gly | Glu 220 | Ala | Tyr | Val | Gln |
| Thr 225 | Gly | Glu | Val | Leu | Thr 230 | Arg | Lys | Gln | Ile | Val 235 | Asp | Glu | Thr | Gly | Leu 240 |
| Ser | Arg | Ala | Thr | Val 245 | Thr | Arg | His | Leu | Ala 250 | Ala | Leu | Arg | Glu | Gln 255 | Gly |
| Ala | Leu | Pro | Glu 260 | Thr |

CORYNEFORM BACTERIA DNA FRAGMENT CONTAINING A GENE RESPONSIBLE FOR THE FUNCTION OF AUTONOMOUS REPLICATION OF PLASMID

BACKGROUND OF THE INVENTION

1. Field of the Invention

The present invention relates to DNA fragment containing a gene which imparts the ability to autonomously replicate to a plasmid vector containing it. More specifically, the present invention relates to a DNA fragment containing such a gene in a plasmid held in a Coryneform bacterium. The DNA fragment of the present invention contains at least one point mutation in the gene region such that a plasmid vector containing it has an increased copy number per Coryneform bacterium. The present invention also provides a method for producing a useful biologically product using such a plasmid vector.

2. Discussion of the Background

Coryneform bacteria, including the genus Brevibacterium, are extremely useful in industry because of their ability to produce amino acids, organic acids, purine nucleotides, etc. In order to enhance the productivity of fermentative products by these Coryneform bacteria, plasmid vectors which employ Coryneform bacteria as host microorganisms have been developed using recombinant DNA techniques.

For example, U.S. Pat. No. 5,185,262 describes plasmid pCRY3 which comprises (1) a DNA region isolated from plasmid pBY503 held in *Brevibacterium stationis* IFO 12144 (FERM BP-2515) which encodes a gene useful for autonomous replication of a plasmid in a Coryneform bacterium; (2) a DNA region containing a drug resistance gene which can be used as a plasmid marker; and (3) a DNA region encoding a gene required for replication in *Escherichia coli*. Unfortunately, when a gene encoding a useful biological product is inserted into pCRY3 and the plasmid is subsequently inserted into a Coryneform bacterium, the biologically useful product is not produced in high levels.

Production is low because the amount of biological product produced is approximately proportional to the copy number of the plasmid vector and the copy number of pCRY3 in a Coryneform bacterium is only 4 to 6.

Accordingly, a plasmid which exhibits a high copy number in a Coryneform bacterium is desirabe so that when a gene encoding a biologically useful product is inserted into the plasmid vector, higher gene dosage effect (in other words, higher expression) of the useful gene can be expected.

SUMMARY OF THE INVENTION

Accordingly, one object of the present invention is to provide a DNA fragment which encodes a gene which allows said plasmid to replicate autonomously in a Coryneform bacterium such that when said DNA fragment is incorporated into a plasmid, it imparts the ability for said plasmid to exist in a Coryneform bacterium in high copy number.

A second object of the present invention is to provide a plasmid containing said DNA fragment.

A third object of the present invention is to provide a Coryneform bacterium containing said plasmid.

A fourth object of the present invention is to provide a method for producing a biologically useful product comprising culturing such a Coryneform bacterium in a culture medium for a time sufficient to produce said biological product.

The present inventors have carried out extensive studies to accomplish the above object. As the result, they have discovered a DNA fragment which contains a gene isolated from the plasmid pBY503 held in *Brevibacterium stationis* IFO 12144 (FERM BP-2515), wherein the gene has at least one point mutation. When this DNA fragment is incorporated into a plasmid and placed in a Coryneform bacterium, the copy number of the plasmid in the Coryneform bacterium increases.

Obviously, numerous modifications and variations of the present invention are possible in light of the above teachings. It is therefore to be understood that within the scope of the appended claims, the invention may be practiced otherwise than as specifically described herein.

DETAILED DESCRIPTION OF THE PREFERRED EMBODIMENT

Figure 1:
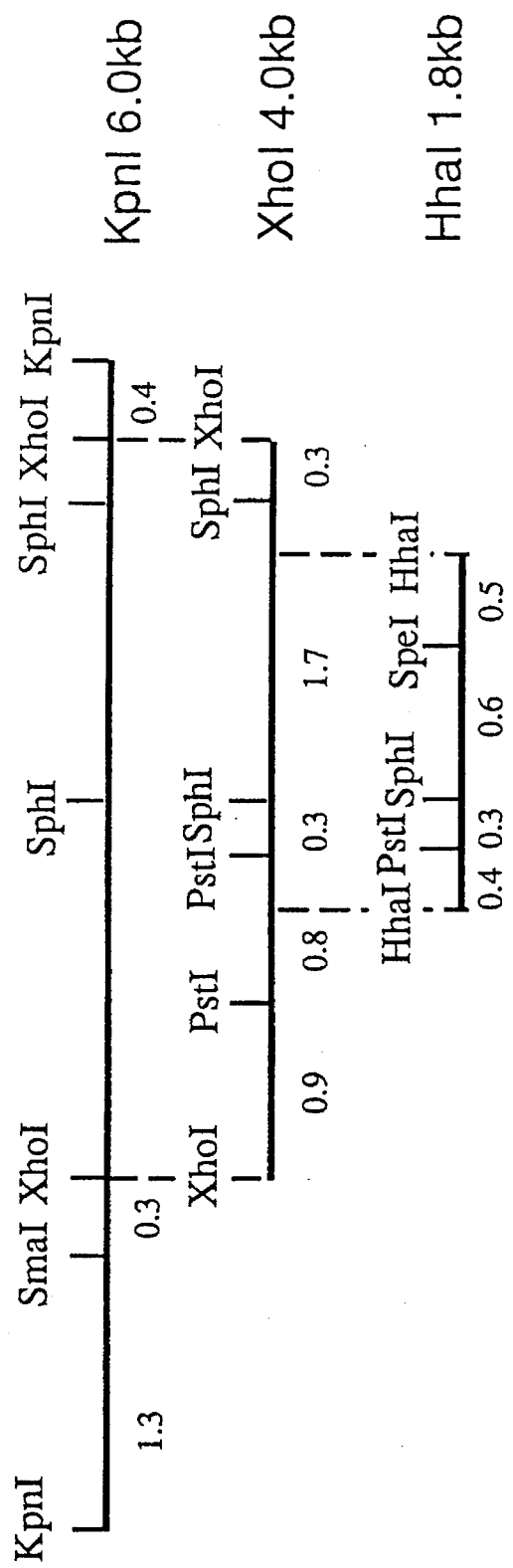
FIG. 1 is a restriction map of the DNA fragment of the present invention.

Hereinafter, a DNA fragment containing a gene responsible for automomous replication of a plasmid in a Coryneform bacterium is referred to as an "autonomous replication gene". A DNA fragment containing such an autonomous replication gene, but which also has a point mutation which increases the copy number of a plasmid containing the DNA fragment in a Coryneform bacterium is referred to as the "autonomous replication DNA fragment exhibiting high copy number".

The DNA fragment of the present invention contains a gene responsible for autonomous replication of a plasmid in a Coryneform bacterium, wherein said gene contains at least one point mutation which increases the copy number of a plasmid containing it in a Coryneform bacterium. A plasmid vector containing the DNA fragment of the present invention has an increased copy number as compared to a plasmid vector containing a DNA fragment encoding the same gene without the point mutation.

In the present specification, the term "copy number" means the number of plasmid molecules (the number of plasmids existing) per cell, and the term "high copy number" means the copy number of the plasmid is higher than that of plasmid pBY503 or pCRY3.

The autonomous replication DNA fragment exhibiting high copy number of the present invention can be synthesized after determination of its nucleotide sequence if the sequence determination is possible. In general, the DNA fragment can be isolated and obtained from the cleaved fragments of a plasmid, said plasmid being prepared by (i) mutagenizing the gene which exists on plasmid pBY503 (see U.S. Pat. No. 5,185,262) having a length of about 15 kb held in *Brevibacterium stationis* IFO 12144 (FERM BP-2515) and which is responsible for the function of autonomous replication in a Coryneform bacterium, to give a modified gene; (ii) introducing the modified gene into a plasmid; and (iii) screening for a plasmid having increased copy number caused by the modification.

The gene which exists on plasmid pBY503 having a length of about 15 kb held in *Brevibacterium stationis* IFO 12144 (FERM BP-2515) and which is responsible for the function of autonomous replication in a Coryneform bacterium can be mutagenized by irradiation with X-, γ- or UV-ray or by exposure to a mutagenic agent such as N-methyl-N'-nitro-N-nitrosoguanidine.

The mutagenized gene can be introduced into any suitable plasmid vector using conventional methods. Preferably, the plasmid vector carries a antibiotic resistance gene which can be used as a marker for selection purposes.

The plasmids containing the mutagenized gene can then be transformed into a suitable Coryneform bacterium using conventional methods such as electroporation. Transformation of a host microorganism with a recombinant plasmid vector can be carried out according to the method known in the art, such as a method described by Satoh et al., *Journal of Industrial Microbiology* (1990) 5:159 (e.g. a method in which pulse wave is passed through a host microorganism); a method described by Calvin and Hanawalt, *Journal of Bacteriology* (1988) 170:2796; and a method described by Ito et al., *Agricultural and Biological Chemistry* (1988) 52:293.

As the host microorganisms which can be transformed with a plasmid vector described above and a plasmid vector prepared by integrating the above useful gene into the plasmid vector of the present invention, there can be employed, for example, Coryneform bacterium such as *Brevibacterium flavum* MJ-233 (FERM BP-1497), *Brevibacterium flavum* MJ-233-AB-41 (FERM BP-1498), *Brevibacterium flavum* MJ-233-ABT-11 (FERM BP-1500), *Brevibacterium flavum* MJ-233-ABD-21 (FERM BP-1499), and the like. These microorganisms have been deposited at Fermentation Research Institute (now National Institute of Bioscience and Human-Technology), Agency of Industrial Science and Technology, 1-3, Higashi 1-chome, Tsukuba-shi, Ibaraki-ken 305, Japan.

In addition to the microorganisms described above, there can also be used as host microorganism, for example *Brevibacterium ammoniagenes* ATCC 6871, ATCC 13745 and ATCC 13746, *Brevibacterium devaricatum* ATCC 14020, *Brevibacterium lactofermentum* ATCC 13869, *Corynebacterium glutamicum* ATCC 31830 and the like. These microorganisms are available from the American Type Culture Collection, 12301 Parklawn Drive, Rockville, Md. 20852.

When a strain of *Brevibacterium flavum* MJ-233 containing the plasmid pBY502 is used as a host microorganism, sometimes transformation is difficult. In such case, it is desirable to remove plasmid pBY502 from the strain. The method for removal of plasmid pBY502 is, for example, to make delete the plasmid naturally by repeating subcultures or to remove the plasmid artificially (See Bact. Rev. (1972) 36:361–402).

Coryneform bacteria containing the mutagenized gene can be selected by cultivating under selective pressures such as by varying the concentrations of an antibiotics.

From those cultivated strains in which the antibiotics-resistancy is increased, strains developing gene dosage effect caused by an increase in the number of plasmid copies can be isolated and analyzed for the copy number of the plasmid. From the strains thus prepared in which antibiotics-resistancy and the number of plasmid copies are increased compared to those in their parent strains, a plasmid is extracted. The plasmid extracted is digested with a suitable restriction enzyme to give an autonomous replication DNA fragment exhibiting high copy number according to conventional methods.

The DNA fragment of the present invention can be inserted into a suitable vector plasmid according to the conventional methods. Preferably, a vector plasmid which carries an antibiotic resistance gene is used such as pHSG398 carrying a chloramphenicol-resistance gene (available from Takara Shuzo Co., Ltd.), pHSG298 carrying a Kanamycin-resistance gene (available from Takara Shuzo Co.,Ltd.), and pBR322 carrying a tetracycline-resistance gene (available from Takara Shuzo Co., Ltd.).

The DNA fragment containing autonomous replication gene of the present invention isolated from pBY503 can be confirmed by: (1) inserting a DNA fragment obtained by digesting an autonomous replication gene-containing plasmid pBY503 with a suitable restriction enzyme into a vector plasmid carrying a antibiotic resistance gene which can be used as a marker; (2) subsequently introducing the resulting vector into a host Coryneform bacterium by a transformation method such as the electroporation method (in which the host Coryneform bacterium and the transformation method is the same as those described afterward); (3) extracting a plasmid DNA from the resulting transformant by any suitable conventional method known in the art such as the alkaline-SDS method (see Maniatis, Eritsch and Sambrook, "Molecular Cloning", p.90–91 (1982)); (4) digesting the extracted plasmid DNA with a suitable restriction enzyme; and (5) subjecting the digested plasmid DNA to analysis.

In this method, the analysis of the copy number of plasmid can be carried out according to the method described in *Journal of Bacteriology* (1982) 152:722, in which chromosomal DNA and plasmid DNA are extracted from a cell and the ratio of the number of molecules between the two kinds of DNA is determined.

The autonomous replication DNA fragment exhibiting high copy number obtained by the above procedure is, for example, a DNA fragment of about 6.0 kb in length which can be obtained by digesting plasmids pCOP1 and pCOP2 with a restriction enzyme Kpn I, wherein plasmids pCOP1 and pCOP2 can be obtained from *Brevibacterium flavum* MJ233 cop1 (FERM BP-4610) and MJ233 cop2 (FERM BP-4611). These strains were obtained by mutagenizing *Brevibacterium flavum* MJ233 GE102 (FERM BP-2513) carrying plasmid pCRY3 with N-methyl-N'-nitro-N-nitrosoguanidine such that the chloramphenicol resistancy increased and the copy number increased about two-times.

In the present specification, the "number of recognition site" is determined by completely digesting a DNA fragment or a plasmid in the presence of the restriction enzyme and then analyzing the number of fragments obtained by 1%-agarose gel electrophoresis or 4%-polyacrylamide gel electrophoresis according to conventional methods.

The "size of the cleaved fragment" is determined electrophoretically by comparing the length of the cleaved fragment against either (i) the standard pattern obtained by applying DNA fragments of known molecular weight prepared by cleaving DNA of λ phage of *Escherichia coli* with restriction enzyme Hind III when 1%-agarose gel electrophoresis is empolyed or (ii) the standard pattern given obtained by applying DNA fragments of known molecular weight prepared by cleaving DNA of φ×174 phage of *Escherichia coli* with restriction enzyme Hae III when 4%-polyacrylamide gel electrophoresis is employed.

The "size of the plasmid" is determined by summing each DNA fragment length of a plasmid using the above-described method for determination of the "size of the cleaved fragment". In determination of the length of each DNA fragment of the present invention, the value given by 1%-agarose gel electrophoresis is employed for the fragment having a length of 1 kb or more, and the value given by 4%-polyacrylamide gel electrophoresis is employed for the fragment having a length of less than 1 kb.

By extracting DNA fragments of determined length by the above manner from the electrophoretic gel, the DNA fragment having desired length can be obtained.

Two kinds of autonomous replication DNA fragments of about 6.0 kb exhibiting high copy number can be prepared by digesting plasmids pCOP1 and pCOP2 with restriction enzyme Kpn I, the number of recognition sites and the length of fragments with various restriction enzymes are identical to each other, as shown below in Table 1.

TABLE 1

| Restriction Enzyme | Number of Recognition Site | Length of Cleaved Fragment (kb) |
|---|---|---|
| Sma I | 1 | 1.3, 4.7 |
| Xho I | 2 | 1.6, 4.0, 0.4 |
| Sph I | 2 | 3.6, 1.7, 0.7 |

In Table 1, the DNA fragments of about 4 kb and about 1.8 kb prepared by further digesting said Kpn I-cleaved DNA fragment of about 6.0 kb with Xho I and Hha I, respectively, are confirmed to have autonomously replication function exhibiting high copy number in the cell. Accordingly, these DNA fragments are involved in the autonomous replication DNA fragments exhibiting high copy number of the present invention.

As described above, the autonomous replication gene or the autonomous replication gene exhibiting high copy number is considered to be contained in the DNA fragment of about 4.0 kb which can be obtained by digesting plasmid pBY503, pCRY3, pCOP1 or pCOP2 with restriction enzyme Xho I and the DNA fragment of about 1.8 kb which can be obtained by digesting each the above plasmids with restriction enzyme Hha I.

In the DNA fragments of about 4.0 kb which are prepared by digesting plasmids pCOP1 and pCOP2 with restriction enzyme Xho I, respectively, the number of recognition sites and the length of fragments given by further digesting with various restriction enzymes are identical to each other, as shown in Table 2 below.

TABLE 2

| Restriction Enzyme | Number of Recognition Site | Length of Cleaved Fragment (kb) |
|---|---|---|
| Pst I | 2 | 0.9, 0.8, 2.3 |
| Sph I | 2 | 2.0, 1.7, 0.3 |

In the DNA fragments of about 1.8 kb which are prepared by digesting plasmids pCOP1 and pCOP2 with restriction enzyme Hha I, respectively, the number of recognition sites and the length of fragments given by further digesting with various restriction enzymes are also identical to each other, as shown in Table 3 below.

TABLE 3

| Restriction Enzyme | Number of Recognition Site | Length of Cleaved Fragment (kb) |
|---|---|---|
| Pst I | 1 | 0.4, 1.4 |
| Sph I | 1 | 0.7, 1.1 |
| Spe I | 1 | 1.3, 0.5 |

On the other hand, in the DNA fragments of about 1.8 kb which are obtained by digesting plasmids pCOP1 and pCOP2 with restriction enzyme Hha I, respectively, and which contain the autonomous replication gene exhibiting high copy number and the DNA fragments of about 1.8 kb which are obtained by digesting plasmids pBY503 and pCRY3 with restriction enzyme Hha I, respectively, and which contain the autonomous replication gene, the nucleotide sequence of each DNA fragment can be determined according to the dideoxy chain termination method (Sanger et al., *Proc. Natl. Acad. Sci. U.S.A.* (1977) 74:5463), in which plasmid pUC18 or pUC19 is used.

The sequences of the DNA fragment of about 1.8 kb obtained from plasmids pCOP1 and pCOP2 are shown in SEQ ID NOS: 1 and 3, respectively, below.

SEQ ID NO:1

```
GCGCAGCCTG ACCATGGACA TGCTTCTACG TTCTTCCACA CTGGTATCTT TTGGTTGCAA    60

TATATATTGC AACCATGCTG GTAAAACAAC TTTTTAGCGT GTCTTGCCCA AAATTACAGT   120

CATGTGATTT ACAGTTGAAA GATACTGAAA ATCAAAGAAG GCCACTCGGC GGCAACCGAA   180

TGACCTTCGC TTATCACCCA GTCCTACCTG GGAGAAAGCA TGTACATGAT TATACCCAAT   240

AGTACGCCCG CGTACCCCAT TTCCGGTTCG CGTGTTAACA CGCCATCACG TTTGCGCCCT   300

GACTGCGCAG GCCTTGATGA CACCCCAGCG AGCACCGTTG ACCGGGACAA GCTGCTCGCA   360

CATCTTGGCC GTACAGCACT GCACGGGTCT ATAAGTCGAA ACTTCAAAGG CGCTTATCGC   420

CTCGTTGTGG ATAAGGAAAC GGGGGAAAAG CGAAGCGTTC CGAACCTTTA CCGCATTGAT   480
```

```
                                                                -continued
TCCGAAAAAC TCGGTCGCTG CGAATACGTC ATGCTGACTA GTAAGCAATA TGCTTCGGTC    540

ATGGTCATAG ACGTTGACCA GATAGGAGAG GCTGGAGGAC ATCCAGAAAA CCTCAACTCC    600

TATGTCAAAG GCGTTATCTG GGTACTTGTG CAGCACGGAA TTGGACCAGC ATGGGCAGGC    660

ATTAATCCGA TTAGTGGTAA AGCGCAGTTT ATTTGGCTTA TTGACCCAGT TTATGCAGGA    720

AAGAATCGTG CGTCCCGGAA TATGGAGCTA CTCAAAGCCA CAAGTCACGA GTTGGGTGAG    780

TTACTGGATC ATGATCCACA TTTTGCGCAT CGGTTTAGCC GGAGTCCTTT TTATACTGGA    840

AAGTCACCGG AGGCTTATCG CTGGTATTGC CAGCATGACC GGGTTATACG CCTCCAAGAC    900

TTTCTAAGGC AGGTGCGCGA G ATG GCG GGA CAA TCC CAG CAC ATT AAA AAC      951
                         Met Ala Gly Gln Ser Gln His Ile Lys Ssn
                          1               5                    10
```

| AAG | CGC | CAG | CAA | TTT | AAC | AGT | GGC | CGT | GAG | CTT | ATT | AAT | GCG | GTC | AAA | 999 |
|---|---|---|---|---|---|---|---|---|---|---|---|---|---|---|---|---|
| Lys | Arg | Gln | Gln | Phe | Asn | Ser | Gly | Arg | Glu | Leu | Ile | Asn | Ala | Val | Lys | |
| | | 15 | | | | | 20 | | | | | 25 | | | | |

| ACT | CGC | CGT | GAA | GAA | GCC | CAA | GCC | TTT | AAA | GCA | CTT | GCT | GAG | GAT | GTC | 1047 |
|---|---|---|---|---|---|---|---|---|---|---|---|---|---|---|---|---|
| Thr | Arg | Arg | Glu | Glu | Ala | Gln | Ala | Phe | Lys | Ala | Leu | Ala | Glu | Asp | VBal | |
| | | | 30 | | | | | 35 | | | | | 40 | | | |

| GAA | AAC | GAG | ATA | AGT | GAA | GAA | ATC | GAT | CAA | TAC | GAC | CCG | GAA | CTA | ATC | 1095 |
|---|---|---|---|---|---|---|---|---|---|---|---|---|---|---|---|---|
| Glu | Asn | Glu | Ile | Ser | Glu | Glu | Ile | Asp | Gln | Tyr | Asp | Pro | Glu | Leu | Ile | |
| | | 45 | | | | 50 | | | | | 55 | | | | | |

| GAC | GGG | GTG | CGC | GTG | CGC | TGG | ATT | AGC | CAA | GGG | GTC | GCA | GCA | CGC | GAC | 1143 |
|---|---|---|---|---|---|---|---|---|---|---|---|---|---|---|---|---|
| Asp | Gly | Val | Arg | Val | Arg | Trp | Ile | Ser | Gln | Gly | Val | Ala | Ala | Arg | Asp | |
| | 60 | | | | | 65 | | | | | 70 | | | | | |

| GAA | ACA | GCG | TTT | AGC | CAC | GCA | CTA | AAA | ATT | GGT | CAC | CGC | CTA | CGC | AAA | 1191 |
|---|---|---|---|---|---|---|---|---|---|---|---|---|---|---|---|---|
| Glu | Thr | Ala | Phe | Ser | His | Ala | Leu | Lys | Ile | Gly | His | Arg | Leu | Arg | Lys | |
| 75 | | | | | 80 | | | | | 85 | | | | | 90 | |

| GCA | GGA | CAA | CGA | CTC | ACA | GAC | GCC | GCC | GTT | ATC | GAT | GCC | TAC | GAG | CAT | 1239 |
|---|---|---|---|---|---|---|---|---|---|---|---|---|---|---|---|---|
| Ala | Gly | Gln | Arg | Leu | Thr | Asp | Ala | Ala | Val | Ile | Asp | Ala | Tyr | Glu | His | |
| | | | | 95 | | | | | 100 | | | | | 105 | | |

| GCC | TAT | AAC | GTT | GCA | CAA | CAA | CAA | GGC | TCA | GCA | GGC | CGA | GAC | AGC | GAA | 1287 |
|---|---|---|---|---|---|---|---|---|---|---|---|---|---|---|---|---|
| Ala | Tyr | Asn | Val | Ala | Gln | Gln | Gln | Gly | Ser | Ala | Gly | Arg | Asp | Ser | Glu | |
| | | | 110 | | | | | 115 | | | | | 120 | | | |

| ATG | CCA | CCC | ATG | CGT | GAC | CAC | CAG | ACC | ATG | GCA | CGA | CGC | GTA | CGC | GGC | |
|---|---|---|---|---|---|---|---|---|---|---|---|---|---|---|---|---|
| Met | Pro | Pro | Met | Arg | Asp | His | Gln | Thr | Met | Ala | Arg | Arg | Val | Arg | Gly | |
| | | 125 | | | | | 130 | | | | | 135 | | | | |

| TAT | GTC | ACC | CAA | TCC | AAA | ACC | AAC | ACA | AGT | CTA | GGA | GCT | AGC | GCT | CCC | 1383 |
|---|---|---|---|---|---|---|---|---|---|---|---|---|---|---|---|---|
| Tyr | Val | Thr | Gln | Ser | Lys | Thr | Asn | Thr | Ser | Leu | Gly | Ala | Ser | Ala | Pro | |
| | | 140 | | | | | 145 | | | | | 150 | | | | |

| GGA | CGC | GTT | ACC | AGC | AGC | GAA | CGC | AAA | GCA | CTG | GCC | ACC | ATG | GGG | CGA | 1431 |
|---|---|---|---|---|---|---|---|---|---|---|---|---|---|---|---|---|
| Gly | Arg | Val | Thr | Ser | Ser | Glu | Arg | Lys | Ala | Leu | Ala | Thr | Met | Gly | Arg | |
| 155 | | | | | 160 | | | | | 165 | | | | | 170 | |

| AAA | GGC | GGA | CAG | AAA | GCA | GCA | CAA | CGC | TGG | AAA | ACC | GAT | CCA | GAA | GGT | 1479 |
|---|---|---|---|---|---|---|---|---|---|---|---|---|---|---|---|---|
| Lys | Gly | Gly | Gln | Lys | Ala | Ala | Gln | Arg | Trp | Lys | Thr | Asp | Pro | Glu | Gly | |
| | | | | 175 | | | | | 180 | | | | | 185 | | |

| CAA | TAC | GCA | CAA | AAT | CAG | CTGCAG | AAA | CTA | AAG | AAA | ACG | CAC | CGG | AAG | | 1527 |
|---|---|---|---|---|---|---|---|---|---|---|---|---|---|---|---|---|
| Gln | Tyr | Ala | Gln | Asn | Gln | Leu Gln | Lys | Leu | Lys | Lys | Thr | His | Arg | Lys | | |
| | | | 190 | | | | 195 | | | | | 200 | | | | |

| AAG | CGG | GTG | GAA | GGA | CAG | ACC | ACG | CGT | GCG | AAG | ATT | CAA | GCC | TTA | ATT | 1575 |
|---|---|---|---|---|---|---|---|---|---|---|---|---|---|---|---|---|
| Lys | Arg | Val | Glu | Gly | Gln | Thr | Thr | Arg | Ala | Lys | Ile | Gln | Ala | Leu | Ile | |
| | | 205 | | | | | 210 | | | | | 215 | | | | |

| GGT | GAA | GCT | TAC | GTG | CAA | ACA | GGC | GAG | GTA | CTT | ACC | CGC | AAA | CAG | ATT | 1623 |
|---|---|---|---|---|---|---|---|---|---|---|---|---|---|---|---|---|
| Gly | Glu | Ala | Tyr | Val | Gln | Thr | Gly | Glu | Val | Leu | Thr | Arg | Lys | Gln | Ile | |
| | | 220 | | | | 225 | | | | | 230 | | | | | |

| GTG | GAT | GAG | ACA | GGA | CTA | TCT | AGA | GCT | ACA | GTG | ACA | CGG | CAT | TTG | GCG | 1671 |
|---|---|---|---|---|---|---|---|---|---|---|---|---|---|---|---|---|
| Val | Asp | Glu | Thr | Gly | Leu | Ser | Arg | Ala | Thr | Val | Thr | Arg | His | Leu | Ala | |
| 235 | | | | 240 | | | | | 245 | | | | | 250 | | |

| | | | | | | | | | | |
|---|---|---|---|---|---|---|---|---|---|---|
| GCA | CTT | CGA | GAA | CAG | GGA | GCA | CTT | CCG | GAA | ACG TAGGGGCTCATACCGTAAGCA | 1725 |
| Ala | Leu | Arg | Glu | Gln 255 | Gly | Ala | Leu | Pro | Glu 260 | Thr | |

ATATACGGTT CCCCTGCCGG TAGGAATGTA GTAATAACCT CTCTTGAAGA AAACCTTGTA 1785

GGGCAAGGCT ACTTATGCTT CCGGGGTTAG TCGTTCTTCT ATTGCGGTGA TGAGTTCTAG 1845

ACCTTTATCT AAGTCCTGGG GGCTGCTGTT GCCGTGCGAG GCTTTGCTGC GC 1897

SEQ ID NO:3

GCGCAGCCTG ACCATGGACA TGCTTCTACG TTCTTCCACA CTGGTATCTT TTGGTTGCAA 60

TATATATTGC AACCATGCTG GTAAAACAAC TTTTTAGCGT GTCTTGCCCA AAATTACAGT 120

CATGTGATTT ACAGTTGAAA GATACTGAAA ATCAAAGAAG GCCACTCGGC GGCAACCGAA 180

TGACCTTCGC TTATCACCCA GTCCTACCTG GGAGAAAGCA TGTACATGAT TATACCCAAT 240

AGTACGCCCG CGTACCCCAT TTCCGGTTCG CGTGTTAACA CGCCATCACG TTTGCGCCCT 300

GACTGCGCAG GCCTTGATGA CACCCCAGCG AGCACCGTTG ACCGGGACAA GCTGCTCGCA 360

CATCTTGGCC GTACAGCACT GCACGGGTCT ATAAGTCGAA ACTTCAAAGG CGCTTATCGC 420

CTCGTTGTGG ATAAGGAAAC GGGGGAAAAG CGAAGCGTTC CGAACCTTTA CCGCATTGAT 480

TCCGAAAAAC TCGGTCGCTG CGAATACGTC ATGCTGACTA GTAAGCAATA TGCTTCGGTC 540

ATGGTCATAG ACGTTGACCA GATAGGAGAG GCTGGAGGAC ATCCAGAAAA CCTCAACTCC 600

TATGTCAAAG GCGTTATCTG GGTACTTGTG CAGCACGGAA TTGGACCAGC ATGGGCAGGC 660

ATTAATCCGA TTAGTGGTAA AGCGCAGTTT ATTTGGCTTA TTGACCCAGT TTATGCAGGA 720

AAGAATCGTG CGTCCCGGAA TATGGAGCTA CTCAAAGCCA CAAGTCACGA GTTGGGTGAG 780

TTACTGGATC ATGATCCACA TTTTGCGCAT CGGTTTAGCC GGAGTCCTTT TTATACTGGA 840

AAGTCACCGG AGGCTTATCG CTGGTATTGC CAGCATGACC GGGTTATACG CCTCCAAGAC 900

TTTCTAAGGC AGGTGCGCGA G ATG GCG GGA CAA TCC CAG CAC ATT AAA AACV 951
              Met Ala Gly Gln Ser Gln His Ile Lys Asn
              1               5                   10

| | | | | | | | | | | | | | | | | |
|---|---|---|---|---|---|---|---|---|---|---|---|---|---|---|---|---|
| AAG | CGC | CAG | CAA | TTT | AAC | AGT | GGC | CGT | GAG | CTT | ATT | AAT | GCG | GTC | AAA | 999 |
| Lys | Arg | Gln 15 | Gln | Phe | Asn | Ser | Gly 20 | Arg | Glu | Leu | Ile | Asn 25 | Ala | Val | Lys | |
| ACT | CGC | CGT | GAA | GAA | GCC | CAA | GCC | TTT | AAA | GCA | CTT | GCT | GAG | GAT | GTC | 1047 |
| Thr | Arg | Arg | Glu 30 | Glu | Ala | Gln | Ala | Phe 35 | Lys | Ala | Leu | Ala | Glu 40 | Asp | Val | |
| GAA | AAcC | GAG | ATA | AGT | GAA | GAA | ATC | GAT | CAA | TAC | GAC | CCG | GAA | CTA | ATC | 1095 |
| Glu | Asn | Glu 45 | Ile | Ser | Glu | Glu | Ile 50 | Asp | Gln | Tyr | Asp | Pro 55 | Glu | Leu | Ile | |
| GAC | GGG | GTG | CGC | GTG | CGC | TGG | ATT | AGC | CAA | GGG | GTC | GCA | CGC | GAC | | 1143 |
| Asp | Gly | Val 60 | Arg | Val | Arg | Trp | Ile 65 | Ser | Gln | Gly | Val | Ala 70 | Arg | Asp | | |
| GAA | ACA | GCG | TTT | AGC | CAC | GCA | CTA | AAA | ATT | GGT | CAC | CGC | CTA | CGC | AAA | 1191 |
| Glu | Thr | Ala | Phe | Ser 80 | His | Ala | Leu | Lys | Ile 85 | Gly | His | Arg | Leu | Arg | Lys 90 | |
| 75 | | | | | | | | | | | | | | | | |

| | | | | | | | | | | | | | | | | |
|---|---|---|---|---|---|---|---|---|---|---|---|---|---|---|---|---|
| GCA | GGA | CAA | CGA | CTC | ACA | GAC | GCC | GCC | GTT | ATC | GAT | GCC | TAC | GAG | CAT | 1239 |
| Ala | Gly | Gln | Arg | Leu 95 | Thr | Asp | Ala | Ala | Val 100 | Ile | Asp | Ala | Tyr | Glu 105 | His | |
| GCC | TAT | AAC | GTT | GCA | CAA | CAA | CAA | GGC | TCA | GCA | CGA | GAC | AGC | GAA | | 1287 |
| Ala | Tyr | Asn | Val 110 | Ala | Gln | Gln | Gln | Gly 115 | Ser | Ala | Arg | Asp | Ser 120 | Glu | | |
| ATG | CCA | CCC | ATG | CGT | GAC | CGC | CAG | ACC | ATG | GCA | CGA | CGC | GTA | CGC | GGC | 1335 |
| Met | Pro | Pro 125 | Met | Arg | Asp | Arg | Gln 130 | Thr | Met | Ala | Arg | Arg 135 | Val | Arg | Gly | |
| TAT | GTC | ACC | CAA | TCC | AAA | ACC | AAC | ACA | AGT | CTA | GGA | GCT | AGC | GCT | CCC | 1383 |
| Tyr | Val 140 | Thr | Gln | Ser | Lys | Thr 145 | Asn | Thr | Ser | Leu | Gly 150 | Ala | Ser | Ala | Pro | |
| GGA | CGC | GTT | ACC | AGC | AGC | GAA | CGC | AAA | GCA | CTG | GCC | ACC | ATG | GGG | CGA | 1431 |
| Gly 155 | Arg | Val | Thr | Ser | Ser 160 | Glu | Arg | Lys | Ala | Leu 165 | Ala | Thr | Met | Gly | Arg 170 | |
| AAA | GGC | GGA | CAG | AAA | GCA | GCA | CAA | CGC | TGG | AAA | ACC | GAT | CCA | GAA | GGT | 1479 |
| Lys | Gly | Gly | Gln | Lys 175 | Ala | Ala | Gln | Arg | Trp 180 | Lys | Thr | Asp | Pro | Glu 185 | Gly | |
| CAA | TAC | GCA | CAA | AAT | CAG | CTG | CAG | AAA | CTA | AAG | AAA | ACG | CAC | CGG | AAG | 1527 |
| Gln | Tyr | Ala | Gln 190 | Asn | Gln | Leu | Gln | Lys 195 | Leu | Lys | Lys | Thr | His 200 | Arg | Lys | |
| AAG | CGG | GTG | GAA | GGA | CAG | ACC | ACG | CGT | GCG | AAG | ATT | CAA | GCC | TTA | ATT | 1575 |
| Lys | Arg | Val 205 | Glu | Gly | Gln | Thr | Thr 210 | Arg | Ala | Lys | Ile | Gln 215 | Ala | Leu | Ile | |
| GAT | GAA | GCT | TAC | GTG | CAA | ACA | GGC | GAG | GTA | CTT | ACC | CGC | AAA | CAG | AT | 1623 |
| Asp | Glu 220 | Ala | Tyr | Val | Gln | Thr 225 | Gly | Glu | Val | Leu | Thr 230 | Arg | Lys | Gln | Ile | |
| GTG | GAT | GAG | ACA | GGA | CTA | TCT | AGA | GCT | ACA | GTG | ACA | CGG | CAT | TTG | GCG | 1671 |
| Val 235 | Asp | Glu | Thr | Gly | Leu 240 | Ser | Arg | Ala | Thr | Val 245 | Thr | Arg | His | Leu | Ala 250 | |
| GCA | CTT | CGA | GAA | CAG | GGA | GCA | CTT | CCG | GAA | ACG | TAGGGGCTCATACCGTAAGCA | | | | | 1725 |
| Ala | Leu | Arg | Glu | Gln 255 | Gly | Ala | Leu | Pro | Glu | Thr 260 | | | | | | |

| | | | |
|---|---|---|---|
| ATATACGGTT CCCCTGCCGG TAGGAATGTA GTAATAACCT CTCTTGAAGA AAACCTTGTA | | | 1785 |
| GGGCAAGGCT ACTTATGCTT CCGGGGTTAG TCGTTCTTCT ATTGCGGTGA TGAGTTCTAG | | | 1845 |
| ACCTTTATCT AAGTCCTGGG GGCTGCTGTT GCCGTGCGAG GCTTTGCTGC GC | | | 1897 |

On the other hand, the sequences of the DNA fragments of about 1.8 kb obtained from plasmids pBY503 pCRY3 are identical to each other, as shown in SEQ. ID. No: 5 below.

SEQ ID No:5

| | |
|---|---|
| GCGCAGCCTG ACCATGGACA TGCTTCTACG TTCTTCCACA CTGGTATCTT TTGGTTGCAA | 60 |
| TATATATTGC AACCATGCTG GTAAAACAAC TTTTTAGCGT GTCTTGCCCA AAATTACAGT | 120 |
| CATGTGATTT ACAGTTGAAA GATACTGAAA ATCAAAGAAG GCCACTCGGC GGCAACCGAA | 180 |
| TGACCTTCGC TTATCACCCA GTCCTACCTG GGAGAAAGCA TGTACATGAT TATACCCAAT | 240 |
| AGTACGCCCG CGTACCCCAT TTCCGGTTCG CGTGTTAACA CGCCATCACG TTTGCGCCCT | 300 |
| GACTGCGCAG GCCTTGATGA CACCCCAGCG AGCACCGTTG ACCGGGACAA GCTGCTCGCA | 360 |
| CATCTTGGCC GTACAGCACT GCACGGGTCT ATAAGTCGAA ACTTCAAAGG CGCTTATCGC | 420 |

```
CTCGTTGTGG ATAAGGAAAC GGGGGAAAAG CGAAGCGTTC CGAACCTTTA CCGCATTGAT    480

TCCGAAAAAC TCGGTCGCTG CGAATACGTC ATGCTGACTA GTAAGCAATA TGCTTCGGTC    540

ATGGTCATAG ACGTTGACCA GATAGGAGAG GCTGGAGGAC ATCCAGAAAA CCTCAACTCC    600

TATGTCAAAG GCGTTATCTG GGTACTTGTG CAGCACGGAA TTGGACCAGC ATGGGCAGGC    660

ATTAATCCGA TTAGTGGTAA AGCGCAGTTT ATTTGGCTTA TTGACCCAGT TTATGCAGGA    720

AAGAATCGTG CGTCCCGGAA TATGGAGCTA CTCAAAGCCA CAAGTCACGA GTTGGGTGAG    780

TTACTGGATC ATGATCCACA TTTTGCGCAT CGGTTTAGCC GGAGTCCTTT TTATACTGGA    840

AAGTCACCGG AGGCTTATCG CTGGTATTGC CAGCATGACC GGGTTATACG CCTCCAAGAC    900
```

TTTCTAAGGC AGGTGCGCGA G ATG GCG GGA CAA TCC CAG CAC ATT AAA AAC    951
                        Met Ala Gly Gln Ser Gln His Ile Lys Asn
                         1               5                    10

AAG CGC CAG CAA TTT AAC AGT GGC CGT GAG CTT ATT AAT GCG GTC AAA    999
Lys Arg Gln Gln Phe Asn Ser Gly Arg Glu Leu Ile Asn Ala Val Lys
                15                  20                  25

ACT CGC CGT GAA GAA GCC CAA GCC TTT AAA GCA CTT GCT GAG GAT GTC   1047
Thr Arg Arg Glu Glu Ala Gln Ala Phe Lys Ala Leu Ala Glu Asp Val
            30                  35                  40

GAA AAC GAG ATA AGT GAA GAA ATC GAT CAA TAC GAC CCG GAA CTA ATC   1095
Glu Asn Glu Ile Ser Glu Glu Ile Asp Gln Tyr Asp Pro Glu Leu Ile
        45                  50                  55

GAC GGG GTG CGC GTG CGC TGG ATT AGC CAA GGG GTC GCA GCA CGC GAC   1143
Asp Gly Val Arg Val Arg Trp Ile Ser Gln Gly Val Ala Ala Arg Asp
    60                  65                  70

GAA ACA GCG TTT AGC CAC GCA CTA AAA ATT GGT CAC CGC CTA CGC AAA   1191
Glu Thr Ala Phe Ser His Ala Leu Lys Ile Gly His Arg Leu Arg Lys
75                  80                  85                  90

GCA GGA CAA CGA CTC ACA GAC GCC GCC GTT ATC GAT GCC TAC GAG CAT   1239
Ala Gly Gln Arg Leu Thr Asp Ala Ala Val Ile Asp Ala Tyr Glu His
                95                  100                 105

GCC TAT ASC GTT GCA CAA CAA CAA GGC TCA GCA GGC CGA GAC AGC GAA   1287
Ala Tyr Asn Val Ala Gln Gln Gln Gly Ser Ala Gly Arg Asp Ser Glu
            110                 115                 120

ATG CCA CCC ATG CGT GAC CGC CAG ACC ATG GCA3CGA CGC GTA3CGC GGC   1335
Met Pro Pro Met Arg Asp Arg Gln Thr Met Ala Arg Arg Val Arg Gly
        125                 130                 135

TAT GTC ACC CAA TCC AAA ACC AAC ACA AGT CTA GGA GCT AGC GCT CCC   1383
Tyr Val Thr Gln Ser Lys Thr Asn Thr Ser Leu Gly Ala Ser Ala Pro
    140                 145                 150

GGA CGC GTT ACC AGC AGC GAA CGC AAA GCA CTG GCC ACC ATG GGG CGA   1431
Gly Arg Val Thr Ser Ser Glu Arg Lys Ala Leu Ala Thr Met Gly Arg
155                 160                 165                 170

AAA GGC GGA CAG AAA GCA GCA CAA CGC TGG AAA ACC GAT CCA GAA GGT   1479
Lys Gly Gly Gln Lys Ala Ala Gln Arg Trp Lys Thr Asp Pro Glu Gly
                175                 180                 185

CAA TAC GCA CAA AAT CAG CTG CAG AAA CTA AAG AAA ACG CAC CGG AAG   1527
Gln Tyr Ala Gln Asn Gln Leu Gln Lys Leu Lys Lys Thr His Arg Lys
            190                 195                 200

AAG CGG GTG GAA GGA CAG ACC ACG CGT GCG AAG ATT CAA GCC TTA ATT   1575
Lys Arg Val Glu Gly Gln Thr Thr Arg Ala Lys Ile Gln Ala Leu Ile
        205                 210                 215

GGT GAA GCT TAC GTG CAA ACA GGC GAG GTA CTT ACC CGC AAA CAG ATT   1623
Gly Glu Ala Tyr Val Gln Thr Gly Glu Val Leu Thr Arg Lys Gln Ile
    220                 225                 230

| | | | | | | | | | | | | | | | | |
|---|---|---|---|---|---|---|---|---|---|---|---|---|---|---|---|---|
|GTG|GAT|GAG|ACA|GGA|CTA|TCT|AGA|GCT|ACA|GTG|ACA|CGG|CAT|TTG|GCG|1671|
|Val|Asp|Glu|Thr|Gly|Leu|Ser|Arg|Ala|Thr|Val|Thr|Arg|His|Leu|Ala| |
|235| | | | |240| | | | |245| | | | |250| |

| | | | | | | | | | | |
|---|---|---|---|---|---|---|---|---|---|---|
|GCA|CTT|CGA3GAA|CAG|GGA|GCA|CTT|CCG|GAA|ACG|TAGGGGCTCATACCGTAAGCA 1725|
|Ala|Leu|Arg Glu|Gln|Gly|Ala|Leu|Pro|Glu|Thr| |
| | | |255| | | | |260| | |

ATATACGGTT CCCCTGCCGG TAGGAATGTA GTAATAACCT CTCTTGAAGA AAACCTTGTA 1785

GGGCAAGGCT ACTTATGCTT CCGGGGTTAG TCGTTCTTCT ATTGCGGTGA TGAGTTCTAG 1845

ACCTTTATCT AAGTCCTGGG GGCTGCTGTT GCCGTGCGAG GCTTTGCTGC GC 1897

Evidently from the nucleotide sequences shown in SEQ ID NOS: 1, 3 and 5 above, the DNA fragments of about 1.8 kb containing the autonomous replication gene or the autonomous replication gene exhibiting high copy numbers comprise 1897 base pairs and contain open reading frames (ORF) composed of 783 base pairs encoding 261 amino acids. When the ORF sequences of the DNA fragments from plasmids pCOP1 and pCOP2 shown in SEQ ID NOS: 1 and 3 are compared to that from plasmids pBY503 and pCRY3 shown in SEQ ID NO: 5 (sometimes referred to as "wild type of sequence"), it is evident that in the ORF sequence of DNA fragment shown in SEQ ID NO: 1, the 1307th nucleotide is mutated from guanine (G) to adenine (A) and, consequently, the corresponding encoded amino acid is changed from arginine (Arg) to histidine (His). In the ORF sequence of the DNA fragment shown in SEQ ID NO: 3, the 1577th nucleotide is mutated from G to A and, consequently, the corresponding encoded amino acid is changed from glycine (Gly) to aspartic acid (Asp).

As the result, it is considered that the mutation of nucleotide sequence in ORF as described above leads to increase in the copy number of plasmids.

Accordingly, the DNA fragment containing the following sequences (SEQ ID NOS: 7, 9 and 11) obtained from the sequences of SEQ ID NOS: 1, 3 and 5 above can also be included in the autonomous replication DNA fragment exhibiting high copy number of the present invention.

SEQ ID NO:7, 9 and 11

GCGCAGCCTG ACCATGGACA TGCTTCTACG TTCTTCCACA CTGGTATCTT TTGGTTGCAA 60

TATATATTGC AACCATGCTG GTAAAACAAC TTTTTAGCGT GTCTTGCCCA AAATTACAGT 120

CATGTGATTT ACAGTTGAAA GATACTGAAA ATCAAAGAAG GCCACTCGGC GGCAACCGAA 180

TGACCTTCGC TTATCACCCA GTCCTACCTG GGAGAAAGCA TGTACATGAT TATACCCAAT 240

AGTACGCCCG CGTACCCCAT TTCCGGTTCG CGTGTTAACA CGCCATCACG TTTGCGCCCT 300

GACTGCGCAG GCCTTGATGA CACCCCAGCG AGCACCGTTG ACCGGGACAA GCTGCTCGCA 360

CATCTTGGCC GTACAGCACT GCACGGGTCT ATAAGTCGAA ACTTCAAAGG CGCTTATCGC 420

CTCGTTGTGG ATAAGGAAAC GGGGGAAAAG CGAAGCGTTC CGAACCTTTA CCGCATTGAT 480

TCCGAAAAAC TCGGTCGCTG CGAATACGTC ATGCTGACTA GTAAGCAATA TGCTTCGGTC 540

ATGGTCATAG ACGTTGACCA GATAGGAGAG GCTGGAGGAC ATCCAGAAAA CCTCAACTCC 600

TATGTCAAAG GCGTTATCTG GGTACTTGTG CAGCACGGAA TTGGACCAGC ATGGGCAGGC 660

ATTAATCCGA TTAGTGGTAA AGCGCAGTTT ATTTGGCTTA TTGACCCAGT TTATGCAGGA 720

AAGAATCGTG CGTCCCGGAA TATGGAGCTA CTCAAAGCCA CAAGTCACGA GTTGGGTGAG 780

TTACTGGATC ATGATCCACA TTTTGCGCAT CGGTTTAGCC GGAGTCCTTT TTATACTGGA 840

AAGTCACCGG AGGCTTATCG CTGGTATTGC CAGCATGACC GGGTTATACG CCTCCAAGAC 900

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TTTCTAAGGC | AGGTGCGCGA | G | ATG<br>Met<br>1 | GCG<br>Ala | GGA<br>Gly | CAA<br>Gln | TCC<br>Ser<br>5 | CAG<br>Gln | CAC<br>His | ATT<br>Ile | AAA<br>Lys | AAC<br>Asn<br>10 | | | | 951 |

| AAG<br>Lys | CGC<br>Arg | CAG<br>Gln | CAA<br>Gln | TTT<br>Phe<br>15 | AAC<br>Asn | AGT<br>Ser | GGC<br>Gly | CGT<br>Arg | GAG<br>Glu<br>20 | CTT<br>Leu | ATT<br>Ile | AAT<br>Asn | GCG<br>Ala | GTC<br>Val<br>25 | AAA<br>Lys | 999 |
|---|---|---|---|---|---|---|---|---|---|---|---|---|---|---|---|---|
| ACT<br>Thr | CGC<br>Arg | CGT<br>Arg | GAA<br>Glu<br>30 | GAA<br>Glu | GCC<br>Ala | CAA<br>Gln | GCC<br>Ala | TTT<br>Phe<br>35 | AAA<br>Lys | GCA<br>Ala | CTT<br>Leu | GCT<br>Ala | GAG<br>Glu<br>40 | GAT<br>Asp | GTC<br>Val | 1047 |
| GAA<br>Glu | AAC<br>Asn | GAG<br>Glu<br>45 | ATA<br>Ile | AGT<br>Ser | GAA<br>Glu | GAA<br>Glu | ATC<br>Ile<br>50 | GAT<br>Asp | CAA<br>Gln | TAC<br>Tyr | GAC<br>Asp | CCG<br>Pro<br>55 | GAA<br>Glu | CTA<br>Leu | ATC<br>Ile | 1095 |
| GAC<br>Asp | GGG<br>Gly<br>60 | GTG<br>Val | CGC<br>Arg | GTG<br>Val | CGC<br>Arg | TGG<br>Trp<br>65 | ATT<br>Ile | AGC<br>Ser | CAA<br>Gln | GGG<br>Gly | GTC<br>Val<br>70 | GCA<br>Ala | GCA<br>Ala | CGC<br>Arg | GAC<br>Asp | 1143 |
| GAA<br>Glu<br>75 | ACA<br>Thr | GCG<br>Ala | TTT<br>Phe | AGC<br>Ser | CAC<br>His<br>80 | GCA<br>Ala | CTA<br>Leu | AAA<br>Lys | ATT<br>Ile | GGT<br>Gly<br>85 | CAC<br>His | CGC<br>Arg | CTA<br>Leu | CGC<br>Arg | AAA<br>Lys<br>90 | 1191 |
| GCA<br>Ala | GGA<br>Gly | CAA<br>Gln | CGA<br>Arg | CTC<br>Leu<br>95 | ACA<br>Thr | GAC<br>Asp | GCC<br>Ala | GCC<br>Ala | GTT<br>Val<br>100 | ATC<br>Ile | GAT<br>Asp | GCC<br>Ala | TAC<br>Tyr | GAG<br>Glu<br>105 | CAT<br>His | 1239 |
| GCC<br>Ala | TAT<br>Tyr | AAC<br>Asn | GTT<br>Val<br>110 | GCA<br>Ala | CAA<br>Gln | CAA<br>Gln | CAA<br>Gln | GGC<br>Gly<br>115 | TCA<br>Ser | GCA<br>Ala | GGC<br>Gly | CGA<br>Arg | GAC<br>Asp<br>120 | AGC<br>Ser | GAA<br>Glu | 1287 |
| ATG<br>Met | CCA<br>Pro | CCC<br>Pro<br>125 | ATG<br>Met | CGT<br>Arg | GAC<br>Asp | CRC<br>Xxx | CAG<br>Gln<br>130 | ACC<br>Thr | ATG<br>Met | GCA<br>Ala | CGA<br>Arg | CGC<br>Arg<br>135 | GTA<br>Val | CGC<br>Arg | GGC<br>Gly | 1335 |
| TAT<br>Tyr | GTC<br>Val<br>140 | ACC<br>Thr | CAA<br>Gln | TCC<br>Ser | AAA<br>Lys<br>145 | ACC<br>Thr | AAC<br>Asn | ACA<br>Thr | AGT<br>Ser | CTA<br>Leu<br>150 | GGA<br>Gly | GCT<br>Ala | AGC<br>Ser | GCT<br>Ala | CCC<br>Pro | 1383 |
| GGA<br>Gly<br>155 | CGC<br>Arg | GTT<br>Val | ACC<br>Thr | AGC<br>Ser | AGC<br>Ser<br>160 | GAA<br>Glu | CGC<br>Arg | AAA<br>Lys | GCA<br>Ala | CTG<br>Leu<br>165 | GCC<br>Ala | ACC<br>Thr | ATG<br>Met | GGG<br>Gly | CGA<br>Arg<br>170 | 1431 |
| AAA<br>Lys | GGC<br>Gly | GGA<br>Gly | CAG<br>Gln | AAA<br>Lys<br>175 | GCA<br>Ala | GCA<br>Ala | CAA<br>Gln | CGC<br>Arg | TGG<br>Trp<br>180 | AAA<br>Lys | ACC<br>Thr | GAT<br>Asp | CCA<br>Pro | GAA<br>Glu<br>185 | GGT<br>Gly | 1479 |
| CAA<br>Gln | TAC<br>Tyr | GCA<br>Ala | CAA<br>Gln<br>190 | AAT<br>Asn | CAG<br>Gln | CTG<br>Leu | CAG<br>Gln | AAA<br>Lys<br>195 | CTA<br>Leu | AAG<br>Lys | AAA<br>Lys | ACG<br>Thr | CAC<br>His<br>200 | CGG<br>Arg | AAG<br>Lys | 1527 |
| AAG<br>Lys | CGG<br>Arg | GTG<br>Val<br>205 | GAA<br>Glu | GGA<br>Gly | CAG<br>Gln | ACC<br>Thr<br>210 | ACG<br>Thr | CGT<br>Arg | GCG<br>Ala | AAG<br>Lys | ATT<br>Ile<br>215 | CAA<br>Gln | GCC<br>Ala | TTA<br>Leu | ATT<br>Ile | 1575 |
| GRT<br>Zzz | GAA<br>Glu<br>220 | GCT<br>Ala | TAC<br>Tyr | GTG<br>Val | CAA<br>Gln | ACA<br>Thr<br>225 | GGC<br>Gly | GAG<br>Glu | GTA<br>Val | CTT<br>Leu | ACC<br>Thr<br>230 | CGC<br>Arg | AAA<br>Lys | CAG<br>Gln | ATT<br>Ile | 1623 |
| GTG<br>Val<br>235 | GAT<br>Asp | GAG<br>Glu | ACA<br>Thr | GGA<br>Gly | CTA<br>Leu<br>240 | TCT<br>Ser | AGA<br>Arg | GCT<br>Ala | ACA<br>Thr | GTG<br>Val<br>245 | ACA<br>Thr | CGG<br>Arg | CAT<br>His | TTG<br>Leu | GCG<br>Ala<br>250 | 1671 |
| GCA<br>Ala | CTT<br>Leu | CGA<br>Arg | GAA<br>Glu | CAG<br>Gln<br>255 | GGA<br>Gly | GCA<br>Ala | CTT<br>Leu | CCG<br>Pro | GAA<br>Glu<br>260 | ACG<br>Thr | TAGGGGCTCATACCGTAAGCA | | | | | 1725 |

|  |  |
|---|---|
| ATATACGGTT CCCCTGCCGG TAGGAATGTA GTAATAACCT CTCTTGAAGA AAACCTTGTA | 1785 |
| GGGCAAGGCT ACTTATGCTT CCGGGGTTAG TCGTTCTTCT ATTGCGGTGA TGAGTTCTAG | 1845 |
| ACCTTTATCT AAGTCCTGGG GGCTGCTGTT GCCGTGCGAG GCTTTGCTGC GC | 1897 | wherein the Rs at the 1307th and 1577th nucleotides in the above nucleotide sequence represent G or A, but both Rs never represent G simultaneously; and the 129th amino acid, Xxx, and the 219th amino acid, Zzz, in the above amino acid sequence represent Arg or His and Gly or Asp, respectively, but Zzz is never Gly if Xxx is Arg.

The autonomous replication DNA fragment exhibiting high copy number may be those isolated from plasmids pCOP1 and pCOP2 or those synthesized using a conventional DNA synthesizer such as "SYSTEM-1 PLUS" available from Beckman Co. Ltd.

In the autonomous replication DNA fragments exhibiting high copy number which have any of the above sequences of the present invention, a part of the nucleotide sequence may be substituted by another nucleotides, may be inserted with another new nucleotides or may lack a part of the nucleotides, unless they are impaired of their autonomous replication function exhibiting high copy number. The derivatives of these nucleotide sequences can also be included in the autonomous replication DNA fragment exhibiting high copy number of the present invention.

The restriction map of the autonomous replication DNA fragment exhibiting high copy number of the present invention described above in detail with various restriction enzymes is shown in FIG. 1.

By introducing the autonomous replication DNA fragment exhibiting high copy number of the present invention into a DNA fragment or a plasmid containing an antibiotic resistance gene which can be used as a marker expressible in a Corynebacterium, there can be prepared an excellent plasmid vector which is autonomously replicable in a Coryneform bacterium exhibiting high copy number and has a high efficiency of the gene expression.

As the plasmid which can be integrated with the autonomous replication DNA fragment exhibiting high copy number of the present invention and contains an antibiotic resistance gene as a marker in a Coryneform bacterium, there can be employed, for example, aforementioned pHSG398 carrying chloramphenicol-resistance gene, pHSG298 carrying kanamycin-resistance gene and pBR322 carrying tetracycline-resistance gene which are all available from Takara Shuzo Co., Ltd.

The method for insertion of the autonomous replication DNA fragment exhibiting high copy numbers of the present invention into a plasmid vector described above is, for example, a method in which plasmid pHSG398 is cleaved by complete digestion or partial digestion with a suitable restriction enzyme, and then the aforementioned autonomous replication DNA fragment exhibiting high copy number (of about 6.0, 4.0 or 1.8 kb in length) is ligated by treating with a ligase and the like.

Preferable examples of the plasmid vector thus constructed include plasmid pCOP1-1.8 having a length of about 4.0 kb which is composed of a DNA fragment of about 1.8 kb obtained from plasmid pCOP1 by digesting with restriction enzyme Hha I and plasmid pHSG398; and plasmid pCOP2-1.8 having a length of about 4.0 kb which is composed of a DNA fragment of about 1.8 kb obtained from plasmid pCOP2 by digesting with restriction enzyme Hha I and plasmid pHSG398.

In both plasmids pCOP1-1.8 and pCOP2-1.8, the number of recognition sites and the length of cleaved fragments with various restriction enzymes are identical to each other, as shown in Table 4 below.

TABLE 4

| Restriction Enzyme | Number of Recognition Site | Length of Cleaved Fragment (kb) |
| --- | --- | --- |
| Eco RI | 1 | 4.0 |
| Kpn I | 1 | 4.0 |
| Bam HI | 1 | 4.0 |
| Sph I | 2 | 0.7, 3.3 |
| Pst I | 2 | 0.4, 3.6 |

The plasmid vectors which contains an autonomous replication DNA fragment exhibiting high copy number and are capable of replicating autonomously in a Coryneform bacterium with high copy number thus prepared can be integrated with DNA fragments containing structural genes encoding various kinds of industrially useful materials. Accordingly, by introducing the plasmid vector in which the above vector containing the autonomous replication DNA fragment exhibiting high copy number is recombined with an useful gene and the like into a host microorganism and culturing the resultant, a useful material encoded by the useful gene can be produced effectively in an industrial scale.

As the DNA fragment containing an useful structural gene capable of integrating into a plasmid vector according to the present invention, there can be employed, for example, a DNA fragment containing a gene which encodes aspartase (E.C.4.3.1.1); a DNA fragment containing at least a gene which encodes tryptophan synthase (E.C.4.2.1.20) and a promoter and an operator which control the expression of the gene; a DNA fragment containing an amino acid biosynthetic gene such as a threonine or isoleucine biosynthetic gene; etc.

Having generally described this invention, a further understanding can be obtained by reference to certain specific examples which are provided herein for purposes of illustration only and are not intended to be limiting unless otherwise specified.

EXAMPLES

Reference Example 1

Construction of a Composite Plasmid pCRY3 Composed of Plasmids pBY503 and pHSG398

(A) Preparation of Plasmid pBY503

Plasmid pBY503 is a plasmid having a molecular weight of about 10 megadaltons (i.e. about 15 kb) which is isolated from *Brevibacterium stationis* IFO 12144 (FERM BP-2515), as described in detail in U.S. Pat. No. 5,185,262. Plasmid pBY503 was prepared by the following method:

In 1 liter of semi-synthetic medium A [which was prepared by dissolving 2 g of urea, 7 g of $(NH_4)_2SO_4$, 0.5 g of $KH_2PO_4$, 0.5 g of $K_2HPO_4$, 0.5 g of $MgSO_4$, 6 mg of $MnSO_4.4-6H_2O$, 6 mg of $FeSO_4.7H_2O$, 2.5 g of yeast extract, 5 g of Casamino acid, 200 μg of thiamin hydrochloride, and 20 g of glucose in deionized water so that the total volume became 1 liter; pH 7.4], *brevibacterium stationis* was cultured until reaching to the late stage of the logarithmic growth phase and harvested its cells. The harvested cells are suspended in 20 ml of a buffer solution [tris(hydroxymethyl)aminomethane 25 mM, EDTA 10 mM, glucose 50 mM] supplemented with lysozyme in a concentration of 10 mg/ml, and the suspension was then reacted at 37° C. for 1 hour. To the reaction solution, was added 40 ml of alkaline-SDS solution [NaOH 0.2N, SDS 1% (w/w)] and then mixed gently. The resulting mixture was allowed to stand at room temperature for 15 min.

Subsequently, to the reaction mixture, was added 30 ml of potassium acetate solution [a 5M-potassium acetate solution 60 ml, acetic acid 11.5 ml, deionized water 28.5 ml], and then fully mixed. The resulting mixture was allowed to stand in ice for 15 min.

The whole lysate was transferred into a centrifugal tube, and subjected to centrifugation at 4° C. for 10 min at 15,000×g, to give a supernatant.

An equal volume of a phenol/chloroform (1:1, v/v) mixed solution was added to the supernatant to suspend. The whole resulting solution was then transferred into a centrifugal tube, and subjected to centrifugation at room temperature for 5 minutes at 15,000×g, to give an aqueous phase. To the resulting aqueous phase, a 2-hold volume of ethanol was added, and allowed to stand at −20° C. for 1 hour, followed by centrifugation at 4° C. for 10 min at 15,000×g. to recover the precipitate.

The precipitate obtained was dried under reducing pressure, and then dissolved in 20 ml of TE buffer solution [Tris 10 mM, EDTA 1 mM; adjusted pH to 8.0 with hydrochloric acid]. To the resulting solution, was added 15 ml of a cesium chloride solution [which was prepared by dissolving 170 g of cesium chloride in 100 ml of TE buffer solution having a 5-hold concentration] and 1 ml of a 10 mg/ml ethidium bromide solution, to adjust the density of the solution to 1.392 g/ml. The resulting solution was subjected to centrifugation at 12° C. for 42 hours at 116,000×g. Plasmid pBY503 was detected as a lower band in the centrifugal tube by UV irradiation. The band was pulled out from the side of the centrifugal tube with a sterilized plastic injector to give a fraction solution containing plasmid DNA.

Subsequently, the fraction solution was treated four times with an equal volume of isoamyl alcohol to extract and remove ethidium bromide, followed by dialyzing against TE solution. To the resulting dialysate solution containing plasmid pBY503 thus prepared, 3M of sodium acetate solution was added in the final concentration of 30 mM, and a 2-hold volume of ethanol was further added. The resulting mixture was allowed to stand at −20° C. for 1 hour. The solution was then subjected to centrifugation at 15,000×g to precipitate DNA. As the result, about 50 μg of DNA of plasmid pBY503 could be recovered.

(B) Preparation of Plasmid pHSG398

Plasmid pHSG398 (available from Takara Shuzo Co., Ltd.) is a plasmid of about 2.2 kb which can not replicate in a Coryneform but can replicate in *Escherichia coli* to express chloramphenicol-resistancy.

(C) Construction of Composite Plasmid pCRY3

0.5 μg of said plasmid pHSG398 (available from Takara Shuzo Co., Ltd.) was reacted with 5 units of restriction enzyme Kpn I at 37° C. for 1 hour to digest the plasmid DNA completely.

2 μg of said plasmid pBY503 DNA prepared in step (A) above was reacted with 1 unit of restriction enzyme Kpn I at 37° C. for 1 hour to digest the plasmid DNA completely.

Both digested DNAs obtained were mixed with each other and heat-treated at 65° C. for 10 min. to inactivate the restriction enzyme. Subsequently, to the resulting mixture were added 50 mM of Tris buffer solution (pH 7.6), 10 mM of MgCl$_2$, 10 mM of dithiothreitol, 1 mM of ATP and 1 unit of T4 DNA ligase (wherein each concentration being given as the final concentration), to fortifying the components, followed by incubating at 16° C. for about 15 hours. By using the solution thus obtained, *Escherichia coli* JM109 competent cell (available from Takara Shuzo Co., Ltd.) were transformed according to the manual written by the producer.

The transformant obtained was cultured in L medium [which was prepared by dissolving 10 g of tryptone, 5 g of yeast extract and 5 g of sodium chloride in deionized water so that the total volume became 1 liter; pH 7.2] supplemented with 30 μg/ml of chloramphenicol, 100 μg/ml of isopropyl-β-D-thiogalactopyranoside (IPTG) and 100 μg/ml of 5-bromo-4-chloro-3-indolyl-β-D-galactopyranoside (X-gal), wherein each concentration being given as the final concentration, at 37° C. for 24 hours. The strains which grew on the medium as white colonies were screened, and each plasmid in the strains was extracted by the alkaline-SDS method (see Maniatis, Eritsch and Sambrook, "Molecular Cloning", p.90–91 (1982)).

(D) Transformation of the Composite Plasmid into a Coryneform

The electropotation method was employed for transformation. *Brevibacterium flavum* MJ-233 (FERM BP-1497) was cultured in 100 ml of said medium A until reaching to the early stage of the logarithmic growth phase. Subsequently, 100 units of penicillin G was added to the medium, and further cultivated with shaking for 2 hours. The cultivated cells were harvested by centrifugation and washed with 20 ml of a solution [sucrose 272 mM, KH$_2$PO$_4$ 7 mM, MgCl$_2$ 1 mM; pH 7.4]. The cells were collected by further centrifugation, and then suspended in 5 ml of the solution for pulse application. 0.75 ml of the cells were mixed with 50 μl of the DNA solution prepared in step (C) above, and then allowed to stand in ice for 20 min. The resulting mixture was treated using Gene Pulser (available from Bio-rad Co.) under the conditions of 2500 volts and 25μ FD. After pulse application, the reacting mixture was further allowed to stand in ice for 20 min. The whole reacting mixture was transferred to 3 ml of medium A described above, and incubated for 1 hour at 30° C. Subsequently, the reacting mixture was inoculated on an agar plate of the above medium A supplemented with chloramphenicol in an amount of 3 μg/ml (as final concentration), and further incubated at 30° C. for 2 to 3 days. From the culture, *Brevibacterium flavum* MJ233 GE102 which exhibiting chloramphenicol-resistancy was screened, from which plasmid was obtained according to the method described in step (A) above. The plasmid obtained was digested with various restriction enzymes listed in Table 5, and the resulting cleaved fragments were measured for their length. The results are shown in Table 5 below.

TABLE 5

| Restriction Enzyme | Number of Recognition Site | Length of Cleaved Fragment (kb) |
| --- | --- | --- |
| Kpn I | 2 | 6.0, 2.2 |
| Sau I | 1 | 8.2 |
| Bam HI | 1 | 8.2 |
| Pst I | 2 | 5.7, 2.5 |

The plasmid characterized by the cleaved fragments with the restriction enzymes described above was named "pCRY3". Evidently from Table 5, by digesting said plasmid pCRY3 with restriction enzyme Kpn I, there can be confirmed a DNA fragment of 6.0 kb containing autonomous replication gene which is isolated from plasmid pBY503, as well as a 2.2 kb DNA fragment of plasmid pHSG398. *Brevibacterium flavum* MJ233 GE102 which has been transformed with a composite plasmid pCRY3 has been deposited at Fermentation Research Institute (now National institute of Bioscience and Human-Technology), Agency of Industrial Science and Technology, (1-3, Higashi 1-chome, Tsukuba-shi, Ibaraki-ken, Japan) under the deposit No. FERM BP-2513 under the Budapest Treaty.

EXAMPLE 1

Isolation of Mutant-type Plasmid Exhibiting High Copy Number from Plasmid pCRY3

(A) Preparation of High Concentration Chloramphenicol-resistant Strain

*Brevibacterium flavum* MJ233 GE102 (FERM BP-2513) strain carrying the plasmid pCRY3 was mutagenized by exposing to 300 μg/ml of N-methyl-N'-nitro-N-nitrosoguanidine at 30° C. for 30 min., and subsequently cultured on an agar plate of the medium A supplemented with chloramphenicol in a concentration of 6 μg/ml, at 33° C. for 5 hours. The resulting culture was spread and cultured on an agar plate of the medium A composed of 36 μg/ml of chloramphenicol and 15 g/l of agar, from which two kinds of strains exhibiting resistance against high concentration of chloramphenicol were screened.

The mutants capable of growing on said medium containing high concentration of chloramphenicol are named "*Brevibacterium flavum* MJ233 cop1" and "*Brevibacterium flavum* MJ233 cop2", respectively.

(B) Confirmation of Number of Plasmid Copies

*Brevibacterium flavum* MJ233 cop1 and cop2, and *Brevibacterium flavum* MJ233 GE102 (FERM BP-2513) are cultured in the medium A until reaching to the late stage of the logarithmic growth phase and harvested their cultured cells. The resulting cells of each strain were suspended in 20 ml of a buffer solution [tris(hydroxymethyt)aminomethane 25 mM, EDTA 10 mM, glucose 50 mM] supplemented with lysozyme in a concentration of 10 mg/ml, and reacted at 37° C. for 1 hour. To the reaction solution, was added 40 ml of an alkaline-SDS solution [NaOH 0.2N, SDS 1% (w/v)], and mixed gently, followed by standing at room temperature for 15 min. Subsequently, 30 ml of potassium acetate solution [a 5M potassium acetate solution 60 ml, acetic acid 11.5 ml, deionized water 28.5 ml] was further added to the resulting reaction solution. After fully mixing, the mixture was allowed to stand in ice for 15 min.

The whole lysate was transferred into a centrifugal tube, and was subjected to centrifugation at 15,000×g to give a supernatant.

To the supernatant, was added an equal volume of a phenol/chloroform (1:1, v/v) mixed solution and suspend. The whole suspension was then transferred into a centrifugal tube, and subjected to centrifugation at room temperature for 5 min. at 15,000×g, to give an aqueous phase. A 2-hold volume of ethanol was added to the aqueous phase, and then allowed to stand at −20° C. for 1 hour. Subsequently, the reaction mixture was subjected to centrifugation at 4° C. for 10 min. at 15,000×g, to recover the precipitate of DNA.

The resulting precipitate was dried under reducing pressure, and then dissolved in 2 ml of TE buffer solution [Tris 10 mM, EDTA 1 mM; adjusted pH to 8.0 with hydrochloric acid].

The plasmid and the chromosomal DNA which had been extracted in the manner described above were isolated individually by 0.8%-agarose gel electrophoresis. The negative film of each sample of the electrophoresis was applied to the densitometer, to determine the ratio between chromosomal DNA and plasmid DNA. The copy number of the plasmid was calculated regarding the molecular weight of the chromosomal DNA as $3.0 \times 10^9$ daltons and the molecular weight of the plasmid as $5.4 \times 10^3$ daltons (i.e. 8.2 kb).

As the result, it was found that 10 to 12 copies of plasmid existed in *Brevibacterium flavum* MJ233 cop1 and MJ233 cop2, whereas 5 to 6 copies of plasmid (i.e. plasmid pCRY3) existed in *Brevibacterium flavum* MJ233 GE102.

(C) Preparation of a 6.0 kb Autonomous Replication DNA Fragment Exhibiting High Copy Number From each of *Brevibacterium flavum* MJ233 cop1 and MJ233 cop2 prepared in step (A) above, a plasmids was extracted according to the same manner as Reference Example 1, step (A), respectively. The resulting plasmid was digested with various restriction enzymes and measured the length of the cleaved fragments. As the result, it was found that, in the plasmids obtained from both strains, the number of the recognition sites and the length of cleaved fragments with each restriction enzyme were identical to each other, and were further identical to those in plasmid pCRY3, as shown in Table 5 described previously.

The plasmids obtained from *Brevibacterium flavum* MJ233 cop1 and MJ233 cop2, which are characterized by existing in 10 to 12 copies per cell and having the number of recognition sites and the length of cleaved fragment with the restriction enzymes shown in Table 5, were named "pCOP1" and "pCOP2", respectively.

Subsequently, plasmids pCOP1 and pCOP2 were digested with restriction enzyme Kpn I to give the autonomous replication DNA fragments exhibiting high copy number which having a length of about 6.0 kb. The resulting DNA fragments were further digested with various restriction enzymes and the cleaved fragments were determined their length. As the result, it was found that, in the DNA fragments obtained from both plasmids, the number of the recognition sites and the length of the cleaved fragments with the restriction enzymes were identical to each other, as shown in Table 1 described previously.

*Brevibacterium flavum* MJ233 cop1 which carries plasmid pCOP1 and *Brevibacterium flavum* MJ233 cop2 which carries plasmid pCOP2 have been deposited at Fermentation Research Institute (now National Institute of Bioscience and Human-Technology), Agency of Industrial Science and Technology (1-3, Higashi 1-chome, Tsukuba-shi, Ibaraki-ken, Japan on Apr. 27, 1993 under the deposit No. FERM P-13619 and FERM P-13620, respectively (transferred to international deposition under the deposit No. FERM BP-4610 and FERM BP-4611, respectively, on Mar. 16, 1994 under the Budapest Treaty).

EXAMPLE 2

Cloning of the 4.0 kb Autonomous Replication DNA Fragment Exhibiting High Copy Number In plasmids pCOP1 and pCOP2 prepared in Example 1, in order to specify the gene regions which are responsible for the function of autonomous replication exhibiting high copy number in a Coryneform, the autonomous replication DNA fragment of about 6.0 kb of each plasmid was further specified. The following procedures were all carried out independently for each plasmid.

1 μg of plasmid was reacted with 1 unit of restriction enzyme Xho I at 37° C. for 1 hour to digest the plasmid DNA completely. The resulting digest was isolated by 0.8%-agarose gel electrophoresis, from which the fraction of DNA fragment having a length of about 4.0 kb was recovered. From this fraction, DNA was extracted and purified, to give about 0.5 μg of DNA. On the other hand, 1 μg of *Escherichia coli* plasmid pHSG398 described in Reference Example 1 was reacted with 1 unit of restriction enzyme Sal I at 37° C. for 1 hour, and subsequently heated at 70° C. for 10 min. to inactivate the enzyme. The enzyme-inactivated solution thus prepared was mixed with the DNA fragment of about 4.0 kb prepared above, and then was added 50 mM of Tris buffer solution (pH 7.6), 10 mM of MgCl$_2$, 10 mM of dithiothreitol, 1 mM of ATP and 1 unit of T4 DNA ligase (wherein each concentration being given as the final concentration). The resulting mixture was reacted at 16° C. for 15 hours to ligate the DNA fragments.

The DNA ligated was introduced into *Brevibacterium flavum* MJ-233 in the same manner as in Reference Example 1, step (D) to transform the bacterium. The resulting transformant was cultured on a solid medium which was prepared by adding 15 g/l of agar to the medium A containing 36 μg/ml of chloramphenicol for 2 to 3 days, to give a high chloramphenicolresistant strain.

The resulting strain carrying a plasmid into which a DNA fragment of about 4.0 kb obtained from plasmid pCOP1 had been introduced was named "*Brevibacterium flavum* MJ233 COP1-4.0", and the resulting strain carrying a plasmid into which a DNA fragment of about 4.0 kb obtained from plasmid pCOP2 had been introduced was named "*Brevibacterium flavum* MJ233 COP2-4.0".

For each of the above-described two kinds of transformant, the copy number of plasmid was calculated in the same manner as in Example 1, step (B), regarding the molecular weight of the plasmid as 4.0×10$^3$ daltons (i.e. 6.2 kb). As the result, it was found that the copy number of the plasmid carried in the individual transformants was 10 to 12.

From each strain, a plasmid DNA was extracted in the same manner as in Reference Example 1, step (A), and subsequently digested with various restriction enzymes to determine the length of cleaved fragment. As the result, it was found that, in the DNA fragments from both plasmids, the number of the recognition sites and the length of cleaved fragments with the restriction enzymes were identical to each other, as shown in Table 6.

TABLE 6

| Restriction Enzyme | Number of Recognition Site | Length of Cleaved Fragment (kb) |
|---|---|---|
| Eco RI | 1 | 6.2 |
| Bam HI | 1 | 6.2 |
| Kpn I | 1 | 6.2 |
| Sph I | 3 | 4.2, 1.7, 0.3 |

The plasmids held in *Brevibacterium flavum* MJ233 COP1-4.0 and MJ233 COP2-4.0, which were characterized by exhibiting 10 to 12 copies per cell and the number of recognition sites and the length of cleaved fragments with the restriction enzymes shown in Table 6, were named "pCOP1-4.0" and "pCOP2-4.0", respectively.

Subsequently, the autonomous replication DNA fragment of about 4.0 kb exhibiting high copy number, which was obtained from each of plasmid pCOP1 and pCOP2 was digested with various restriction enzymes to determine the length of cleaved fragments. As the result, it was found that, in the DNA fragments from both plasmids, the number of the recognition sites and the length of the cleaved fragments by the restriction enzymes were identical to each other, as shown in Table 2 described previously.

EXAMPLE 3

Cloning of a 1.8 kb Autonomous Replication DNA Fragment Exhibiting High Copy Number 1 μg of each of plasmid pCRY3 prepared in Reference Example 1 and plasmids pCOP1 and pCOP2 prepared in Example 1 was digested completely by reacting with 1 unit of restriction enzyme Kpn I for 1 hour. The resultant was isolated by 0.8% agarose gel electrophoresis. In this step, a digested product of *Escherichia coli* λ phage DNA with restriction enzyme III was also loaded onto the electrophoresis simultaneously with the sample as a size marker. The agarose fraction containing a DNA fragment of about 6.0 kb in length which is responsible for the function of autonomous replication of plasmid was recovered from the gel applied to the electrophoresis, to extract a DNA fragment of about 6.0 kb therefrom.

0.8 μg of the resulting DNA fragment of about 6.0 kb was partially digested by reacting with 0.1 unit of restriction enzyme Hha I at 37° C. for 30 min. Subsequently, the reaction solution containing the digestion products was heat-treated at 70° C. for 10 min to inactivate the enzyme in the solution.

On the other hand, 0.5 μg of *Escherichia coli* plasmid pHSG398 described previously was digested completely by reacting with 0.5 unit of restriction enzyme Acc I at 37° C. for 1 hour. Subsequently, the reaction solution containing the digestion products was also heat-treated at 70° C. for 10 min, to inactivate the enzyme in the solution.

Both of the resulting solutions containing the digestion products were mixed with each other. Into the mixed solution, were added 50 mM of Tris buffer solution (pH 7.6), 10 mM of dithiothreitol, 1 mM of ATP, 10 mM of MgCl$_2$ and 1 unit of T4 DNA ligase (wherein each concentration being given as the final concentration), and the resulting mixture was reacted at 16° C. for 15 hours to ligate the DNA fragments.

The ligated plasmid DNA thus prepared was introduced into a Coryneform by the electroporation method in the same manner as in Reference Example 1, step (D) to transform the bacterium. The resulting transformant was cultivated in the medium A described previously. Subsequently, the individual bacteria cells transformed with the DNAs from plasmids pCOP1 and pCOP2, respectively, were inoculated on an agar plate of the medium A supplemented with chloramphenicol in the final concentration of 30 μg/ml. Likewise, the bacteria cells transformed with the DNA from plasmid pCRY3 were inoculated on an agar plate of the medium A supplemented with chloramphenicol in the final concentration of 5 μg/ml. Each plate was then cultivated at 30° C. for 2 or 3 days to give a chloramphenicol-resistant strain.

The three kinds of chloramphenicolresistant strains which appeared were cultivated independently in 1 liter of the medium A until reaching to the late stage of the logarithmic growth phase, and the cells were then harvested. The resulting cells were suspended in 20 ml of a buffer solution [25 mM Tris(hydroxymethyl)aminomethane, 10 mM EDTA, 50 mM glucose] supplemented with lysozyme in a concentration of 10 mg/ml, and reacted at 37° C. for 1 hour. To the reaction solution, was added 40 ml of alkaline-SDS solution [0.2N NaOH, 1% (w/v) SDS]. They were mixed gently and then allowed to stand at room temperature for 15 min. Subsequently, to the reaction solution, was added 30 ml of a potassium acetate solution [60 ml of a 5M-potassium acetate solution, 11.5 ml of acetic acid, 28.5 ml of deionized water]. They were fully mixed and then were allowed to stand in ice for 15 min.

The whole lysate was transferred into a centrifugal tube, and then subjected to centrifugation at 4° C. for 10 min. at 15,000×g to give a supernatant. To the resulting supernatant, was added an equal volume of a phenol/chloroform solution (1:1, v/v). After suspension, the mixture was transferred into a centrifugal tube, and then was subjected to centrifugation at room temperature for 5 min. at 15,000×g to recover its aqueous phase. Ethanol was added to the aqueous phase in a 2-hold amount. After leaving to stand at −20° C. for 1 hour, the mixture was subjected to centrifugation at 4° C. for 10 min. at 15,000×g, and then the precipitate was recovered therefrom. The resulting precipitate contained a chromosomal DNA and a plasmid DNA. The precipitate was dried under reducing pressure, and then dissolved in 2 ml of TE buffer solution [10 mM Tris, 1 mM EDTA; adjusted pH to 8.0 with hydrochloric acid], to give a test sample.

The sample obtained by the above procedures, which containing the extracted DNAs, was applied to 0.8% agarose gel electrophoresis to measure the molecular weight of the DNAs. As the result, two bands of a chromosomal DNA having $3.0 \times 10^9$ daltons and a plasmid DNA having $2.6 \times 10^3$ daltons (4.0 kb) could be confirmed. Accordingly, it was confirmed that, in the resulting plasmid, the DNA fragment of about 1.8 kb which was obtained by cleaving each of plasmid pCRY3, pCOP1 and pCOP2 with restriction enzyme Hha I (i.e. an autonomous replication DNA fragment exhibiting high copy number) was inserted into the 2.2 kb DNA fragment of plasmid pHSG398.

The three kinds of plasmids thus obtained, in which the three kinds of DNA fragments of about 1.8 kb obtained by digested with restriction enzyme Hha I were introduced, respectively, were digested with various restriction enzymes to determine the length of the cleaved fragments. As the result, it was found that, in the three kinds of plasmids, the number of recognition sites and the length of cleaved fragments with the restriction enzymes were identical to one another, as shown in Table 4 described previously.

The plasmids characterized by containing the 1.8 kb DNA fragment obtained from each of plasmids pCOP1 and pCOP2 and exhibiting the cleaved fragments shown in Table 4 were named "pCOP1-1.8" and "pCOP2-1.8", respectively. Likewise, the plasmid characterized by containing the 1.8 kb DNA fragment obtained from plasmid pCRY3 and exhibiting the cleaved fragments shown in Table 4 was named "pS-1".

The plasmids and the chromosomal DNA obtained by the same manner as in Example 1, step (B) were subjected to the agarose gel etectrophoresis, to determined the copy number of the plasmids by calculating regarding the molecular weight of the chromosomal DNA as $3.0 \times 10^9$ daltons and that of plasmid as $2.6 \times 10^3$ daltons (4.0 kb). As the result, it was found that the copy number of plasmid was 10 to 12 in the plasmids pCOP1-1.8 and pCOP2-1.8, whereas that was 5 to 6 in the plasmid pS-1.

On the other hand, the autonomous replication DNA fragments of about 1.8 kb obtained by digesting plasmids pCOP1 and pCOP2 DNAS with restriction enzyme Hha I were further digested with various restriction enzymes to determine the length of cleaved fragments. As the result, it was found that, in the DNA fragments obtained from both plasmids, the number of recognition sites and the length of cleaved fragments with the restriction enzymes were identical to each other, as shown in Table 3 described previously.

*Brevibacterium flavum* COP1-1.8 and COP2-1.8 which carrying plasmids pCOP1-1.8 and pCOP2-1.8, respectively, have been deposited under the deposit No. FERM P-13506 and FERM P-13507, respectively, at Fermentation Research Institute (now National Institute of Bioscience and Human-Technology), Agency of Industrial Science and Technology (1-3, Higashi 1-chome, Tsukuba-shi, Ibaraki-ken, Japan), on Mar. 4, 1993 (transferred to international deposition under the deposit No. FERM BP-4608 and FERM BP-4609, respectively, under the Budapest Treaty, on Mar. 16, 1994).

EXAMPLE 4

Determination of Mutation Site in Mutagenized Plasmid Exhibiting High Copy Number The nucleotide sequences of the DNA fragments of about 1.8 kb of Example 3 obtained by digesting with restriction enzyme Hha I were determined according to the dideoxy chain termination method [see Sanger, F., Proc. Natl. Acad. Sci. U.S.A., 74, 5463 (1977)]. The nucleotide sequences of the DNA fragments of about 1.8 kb obtained from plasmids pCOP1, pCOP2 and pS-1 were shown in SEQ ID Nos: 1 to 3, respectively, which were described previously.

Each sequence comprises 1897 bases and contains the open reading frame which encodes 261 amino acids, which is assumed to encode the replication protein essential to replication of plasmid. By comparing the sequences obtained from plasmids pCOP1 and pCOP2 to the sequence obtained from plasmid pS-1, it was found that, in the open reading frames, the 1307th base G was mutated into A, which leads to mutation of the corresponding amino acid encoded by the site from Arg to His in the sequence from pCOP1; whereas, the 1577th base G was mutated into A, which leads to mutation of the corresponding amino acid encoded by the site from Gly to Asp in the sequence from pCOP2.

EXAMPLE 5

Cloning of a DNA Fragment Containing a Gene Obtained from *Brevibacterium flavum* MJ-233 which Encoding Aspartase, and Preparation of Plasmids pCOP1-1.8-Asp and pCOP2-1.8-Asp (A) Extraction of Whole DNA of *Brevibacterium flavum* MJ-233

*Brevibacterium flavum* MJ-233 (FERM BP-1497) was cultivated in 1 liter of the medium A described previously until reaching to the late stage of the logarithmic growth phase, and the cultivated cells were then collected. The resulting cells were suspended in 15 ml of a solution [10 mM NaCl, 20 mM Tris buffer solution (pH 8.0), 1 mM EDTA.2Na] supplemented with lysozyme in a concentration of 10 mg/ml. Proteinase K was added to the suspension in the final concentration of 100 μg/ml, and the resulting mixture was then incubated at 37° C. for 1 hour. Sodium dodecylsulfate was further added to the mixture, and then incubated at 50° C. for 6 hours to lyse. To the resulting lysate, was added an equal volume of a phenol/chloroform solution 1:1, v/v), and the resulting mixture was shaken gently at room temperature for 10 min. The whole mixture was subjected to centrifugation at 10° to 12° C. for 10 min. at 5,000×g, to give a supernatant fraction. To the supernatant, sodium acetate was added in the final concentration of 0.3M, and then a 2-hold amount of ethanol was further added gently thereto. The DNA which was present between the aqueous phase and the ethanol phase was taken out by entwining using a glass stick, washed with a 70% ethanol solution and then air-dried. To the resulting DNA, was added 5 ml of a solution [Tris buffer solution (pH 7.5) 10 mM, EDTA.2Na 1 mH]. After standing at 4° C. overnight, the resulting solution was subjected to various experiments as follows.

(B) Construction and Screening of a Recombinant Cosmid Containing Aspartase Gene 90 μl of the whole DNA solution of *Brevibacterium flavum* MJ-233 obtained in step (A) above was digested partially by reacting with 1 unit of restriction enzyme Sau 3AI at 37° C. for 20 min. The partially digested DNA was mixed with cosmid pWE15 (available from Stratagene Co.) which had been digested with restriction enzyme Bam HI and then dephosphorylated. To the resulting mixture, were added 50 mM of Tris buffer solution (pH 7.6), 10 mM of dithiothreitol, 1 mM of ATP, 10 mM of $MgCl_2$ and 1 unit of T4 DNA ligase (wherein each concentration being given as the final concentration), and then reacted at 16° C. for 15 hours to ligate the cleaved DNAs.

Using the resulting cosmid solution obtained by the above procedure and λ DNA in vitro Packaging Kit (available from Takara Shuzo Co., Ltd.), the transduction into *Escherichia coli* was carried out according to the conventional method. The *Escherichia coli* used was an aspartase gene-delation mutant, *Escherichia coli* K-12JRG1114 (aspA23) [wherein the word in the parenthesis represents the aspartase genetic type; see Journal of General Microbiology, 130, 1271–1278 (1984)].

The *Escherichia coli* JRG1174 strain which was a transducted strain described above was spread on an agar plate of a selective medium [which was prepared by dissolving 7 g of $K_2HPO_4$, 2 g of $KH_2PO_4$, 1 g of $(NH_4)_2SO_4$, 0.1 g of $MgSO_4.7H_2O$, 30 mM of L-sodium glutamate and 16 g of agar in 1 liter of deionized water] supplemented with 50 mg of ampicillin. The strain grown on the medium plate, which had held a cosmid containing a aspartase-encoding gene, was cultivated in a liquid medium according to the conventional method, and the cosmid DNA was extracted therefrom. The cosmid extracted was digested with a restriction enzyme, and the resultant was subjected to agarose gel electrophoresis. As the result, it was found that the cosmid composed of a DNA fragment having a length of about 8.8 kb from cosmid pWE15 and a DNA fragment having a length of about 30 kb. The present inventors named this cosmid as "pWE15-Asp".

(C) Subcloning of the DNA Fragment Containing Aspartase Gene into Plasmids pS-1, pCOP1-1.8 and pCOP2-1.8

The digested product of cosmid pWE15-Asp obtained in step (B) above with restriction enzyme Eco RI was mixed with the digested product of each of plasmids pS-1, pCOP1-1.8 and pCOP2-1.8 obtained in Example 3 with restriction enzyme Eco RI, respectively. To the resulting mixture, were added 50 mM of Tris buffer solution (pH 7.6), 10 mM of dithiothreitol, 1 mM of ATP, 10 mM of $MgCl_2$ and 1 unit of T4 DNA ligase (wherein each concentration being given as the final concentration), and then reacted at 16° C. for 15 hours to ligate the digested DNAs.

*Escherichia coli* K-12JRG1114 (aspA23) strain was transformed using the plasmid mixed solution above by the calcium chloride transformation method [see Journal of Molecular Biology, 53, 159 (1970)]. The resulting transformant was spread on an agar plate of a selective medium [which was prepared by dissolving 7 g of $K_2HPO_4$, 2 g of $KH_2PO_4$, 1 g of $(NH_4)_2SO_4$, 0.1 g of $MgSO_4.7H_2O$, 30 mM of L-sodium glutamate and 16 g of agar in 1 liter of deionized water] supplemented with 50 mg of chloramphenicol. The strain grown on the medium plate was cultivated in a liquid medium according to the conventional method, and then the plasmid DNA was extracted therefrom in the same manner as in Example 1. The plasmid extracted was digested with a restriction enzyme, and the resultant was subjected to agarose gel electrophoresis. As the result, a inserted DNA fragment having a length of about 2.4 kb, i.e. an aspartase gene fragment, could be confirmed in plasmids pS-1, pCOP1-1.8 and pCOP2-1.8.

The length of the cleaved fragments of these plasmids with various restriction enzymes are shown in Table 7 below.

TABLE 7

| Restriction Enzyme | Number of Recognition Site | Length of Cleaved Fragment (kb) |
| --- | --- | --- |
| Eco RI | 2 | 4.0, 2.4 |
| Kpn I | 2 | 5.3, 1.1 |
| Xho I | 2 | 5.7, 0.7 |

The plasmids characterized by the cleaved fragment with the above restriction enzymes were named "pS-1-Asp", "pCOP1-1.8-Asp" and "pCOP2-1.8-Asp", respectively.

EXAMPLE 6

Production of L-Asp by *Brevibacterium flavum* Carrying pCOP1-1.8-Asp and pCOP2-1.8-Asp Plasmids pS-1-Asp, pCOP1-1.8-Asp and pCOP2-1.8-Asp, which were obtained in Example 5, were introduced into *Brevibacterium flavum* MJ233 (FERM BP-1497), respectively, to give transformants. The resulting transformants were named "*Brevibacterium flavum* MJ233-S-Asp", "*Brevibacterium flavum* MJ233-COP1-Asp" and "*Brevibacterium flavum* MJ233-COP2-Asp", respectively.

Subsequently, to 100 ml of the medium A described previously which was dividedly introduced into a 500-ml Erlenmeyer flask and sterilized and then supplemented with 6 μg/ml of chloramphenicol, were inoculated the three kinds of transformed strains above, respectively. After adding glucose in the final concentration of 5 g/liter, the medium was cultivated with shaking at 33° C. for 2 days.

1 liter of a main culture medium [which was prepared by dissolving 5% of glucose, 2.3% of ammonium sulfate, 0.05% of $KH_2PO_4$, 0.05% of $K_2HPO_4$, 0.05% of $MgSO_4.7H_2O$, 20 ppm of $FeSO_4.7H_2O$, 20 ppm of $MnSO_4.nH_2O$, 200 μg/l of biotin, 100 μg/l of thiamin hydrochloride, 0.3% of Casamino acid and 0.3% of yeast extract in deionized water so that the final volume became 1 liter], and then sterilized by autoclaving at 120° C. for 20 min. Subsequently, each of the pre-culture liquids obtained above was added to the medium in a volume of 20 ml, and cultivated for 24 hours under the conditions of a rotation speed of 1000 rpm, an aeration amount of 1 vvm, temperature of 33° C. and pH 7.6.

After completion of the cultivation, the resulting culture liquid was subjected to centrifugation at 4000 rpm for 15 min. to harvest cells. The cells were then suspended in deionized water to prepare a cell suspension which showing the O.D. value (optical density, i.e. absorbance value at the wave length of 610 nm) of 50, which was used as the test solution.

50 ml of a reaction solution having a composition shown in Table 8 below was reacted at 45° C. for 5 hours to produce L-aspattic acid. Then, the reaction solution was subjected to centrifugation at 4000 rpm for 15 min. to give a supernatant. The production amount of aspartic acid in the supernatant was determined by the microbiological assay using *Leuconostoc mesenteroides* ATCC 8042.

The results are shown in Table 9 below, as relative values to the amount produced by MJ233-S-Asp strain which being. defined as 1.

TABLE 8

| | |
|---|---|
| Fumaric acid | 5 g |
| MgSO$_4$.7H$_2$O | 0.1 g |
| Polyoxyethylene(20)sorbitan monolaurate | 0.05 ml |
| Ammonia (28%) | 14 ml |
| Test solution | 10 ml |
| Total | 50 ml (pH 9.4) |

TABLE 9

| Test strain | Amount of Produced Aspartic Acid (Relative value) |
|---|---|
| *Brevibacterium flavum* MJ233-S-Asp | 1 |
| *Brevibacterium flavum* MJ233-COP1-Asp | 3 |
| *Brevibacterium flavum* MJ233-COP2-Asp | 3 |

As shown in Table 9, by using the strains which are transformed with plasmids produced by introducing aspartase gene into the plasmids pCOP1-1.8 and pCOP2-1.8 exhibiting high copy number of the present invention, respectively, L-aspartic acid can be produced-in higher efficiency than in the conventional methods.

EXAMPLE 7

Cloning of a DNA Fragmnent Containing a Tryptophan Synthase Gene Isolated from *Brevibacterium flavum* MJ233, and Construction of Plasmids pCOP1-1.8-trp and pCOP2-1.8-trp Containing the Tryptophan Synthase Gene (A) Preparation of a DNA Fragment Containing Tryptophan Bio-synthesis Genes 25 μg of a chromosomal DNA of *Brevibacterium flavum* prepared in Example 5, step (A) above was reacted with 50 units of restriction enzyme Bam HI at 37° C. for 1 hour, to give a Bam HI-digestion solution of the chromosomal DNA. The resulting solution was mixed with a digestion solution which had been prepared by reacting 1 μg of plasmid pBR322 (available from Takara Shuzo Co., Ltd.) with restriction enzyme Bam HI at 37° C. for 1 hour. To the resulting mixture, were added 50 mM of Tris buffer solution (pH 7.6), 10 mM of dithiothreitol, 1 mM of ATP, 10 mM of MgCl$_2$ and 1 unit of T4 DNA ligase (wherein each concentration being given as the final concentration), and reacted at 16° C. for 15 hours to ligate the digested DNAs.

Using the resulting solution, a *Escherichia coli* mutant, ATCC 23718 (a tryptophan synthase gene-deficient mutant; i.e. a tryptophan-requiring mutant) was transformed according to the conventional method [see Mandel and Higa, *J. Mol. Biol.* (1970) 530:159]. The resulting transformant was spread on an agar plate of a selective medium [which was prepared by dissolving 7 g of K$_2$HPO$_4$, 2 g of KH$_2$PO$_4$, 1 g of (NH$_4$)$_2$SO$_4$, 0.1 g of MgSO$_4$.7H$_2$O, 30 mM of L-sodium glutamate and 16 g of agar in deionized water so that the final volume became 1 liter] supplemented with 50 μg/ml of ampicillin.

The strain which had grown on the medium was inoculated in the above medium L supplemented with ampicillin in the final concentration of 50 μg/ml, and then cultivated at 37° C. for 7 hours. The cultivated solution was subjected to centrifugation at 4° C. for 10 min. at 8,000×g to harvest cells.

From the cell harvested, a plasmid DNA was extracted by the alkaline-SDS method [see Maniatis, Fritsch, and Sambrook; "Molecular Cloning", p.90–91, (1982)]. The plasmid was digested with restriction enzyme Bam HI. By applying the resulting cleaved fragments to agarose gel electrophoresis, the insertion of about 12.3 kb was confirmed at the Bam HI restriction site of plasmid pBR322.

(B) Complementation Test against a Tryptophan-requiring *Escherichia coli* Mutant Using the plasmid solution prepared in step (A) above, *Escherichia coli* strains ATCC 23720 (trpD), ATCC 23719 (trpC), ATCC 23718 (trpB) and ATCC 23717 (trpA), which being tryptophan-requiring mutants having no step for tryptophan biosynthesis, were transformed, to give transformants which could grow on the selective medium described previously in a frequency of about 10$^5$ cells/μg of DNA for each mutant.

As the result, it was confirmed that the plasmid prepared in step (B) above contained the tryptophan biosynthetic genes composed of trpE, trpD, trpC, trpB and trpA on its Bam HI-Bam HI DNA fragment of about 12.3 kb. The plasmid was named "pBR322-trpO".

(C) Subcloning of a DNA Fragment Containing a Structural Gene for Tryptophan Synthase into Plasmid pKK223-3

A DNA fragment containing a structural gene for tryptophan synthase, which being contained in plasmid pBR322-trpO prepared in step (B) above, was subcloned into a tac expression vector pKK233-3 (available from Pharmacia Co.) in the manner as described below, to specify the DNA fragment.

The digested product of plasmid pBR322-trpO obtained in step (C) with restriction enzymes Eco RV and Bam HI was mixed with the digested product of the tac expression vector pKK223-3 with restriction enzyme Sma I. The resulting mixture was treated with S1 nuclease to render the ends of the digested products flush. Subsequently, 50 mM of Tris buffer solution (pH 7.6), 10 mM of dithiothreitol, 1 mM of ATP, 10 mM of MgCl$_2$ and 1 unit of T4 DNA ligase were added to the mixture, and then reacted at 16° C. for 15 hours to ligate the digested DNAs.

Using the resulting solution, a strain of *Escherichia coli* K-12 (a tryptophan synthase gene-deficient mutant; i.e. a tryptophan-requiring strain) was transformed according to the conventional method [see Mandel and Higa; *J. Mol. Bio.* (1970) 53:159]. The resulting transformant was spread on an agar plate of a selective medium [which was prepared by dissolving 7 g of K$_2$HPO$_4$, 2 g of KH$_2$PO$_4$, 1 g of (NH$_4$)$_2$SO$_4$, 0.1 g of MgSO$_4$.7H$_2$O, 2 g of glucose and 16 g of agar in deionized water so that the final volume became 1 liter] supplemented with 50 μg/ml of ampicillin.

The strain which had grown on the selective medium was inoculated in the medium L supplemented with ampicillin in the final concentration of 50 μg/ml, and then cultivated at 37° C. for 7 hours. The cultivated solution was subjected to centrifugation at 4° C. for 10 min. at 8,000×g, to harvest cells.

From the cell harvested, a plasmid DNA was extracted by the alkaline-SDS method. The plasmid was digested with a restriction enzyme. By applying the resultant to agarose gel electrophoresis, not only the DNA fragment of 4.6 kb obtained from plasmid pKK223-3 but also the inserted DNA fragment of about 3.7 kb were confirmed.

The plasmid thus prepared was named "pBR322-trpAB".

Subsequently, the digested product of plasmid pBR322-trpAB with restriction enzyme Bam HI was mixed with each of the digested products of plasmids pS-1, pCOP1-1.8 and pCOP2-1.8 with restriction enzyme Bam HI. The resulting mixture was treated under the conditions described above to ligate the digested DNAs.

Using the resulting mixed solution, a strain of *Escherichia coli* K-12 (a tryptophan synthase gene-deficient mutant; i.e. a tryptophan-requiring strain) was transformed according to the conventional method. The resulting transformant was spread on an agar plate of a selective medium [which was prepared by dissolving 7 g of $K_2HPO_4$, 2 g of $KH_2PO_4$, 1 g of $(NH_4)_2SO_4$, 0.1 g of $MgSO_4.7H_2O$, 2 g of glucose and 16 g of agar in deionized water so that the final volume became 1 liter] supplemented with 50 µg/ml of chloramphenicol.

The strain which had grown on the selective medium cultivated in a liquid medium, and plasmid DNA was extracted from the culture liquid. The plasmid was digested with restriction enzyme Bam HI. By applying the resulting cleaved fragments to agarose gel electrophoresis, not only the 4.0 kb DNA fragment obtained from each of plasmid pS-1, pCOP1-1.8 and pCOP2-1.8, but also the inserted DNA fragment of about 3.9 kb (which was a DNA fragment containing a tac promoter DNA of pKK223-3 and a DNA fragment of tryptophan synthase gene) were confirmed.

The length of cleaved fragments of these plasmids with various restriction enzymes are shown in Table 10 below.

TABLE 10

| Restriction Enzyme | Number of Recognition Site | Length of Cleaved Fragment (kb) |
|---|---|---|
| Bam HI | 2 | 4.0, 3.9 |
| Sal I | 2 | 6.8, 1.1 |
| Kpn I | 1 | 7.9 |

The plasmids characterized by the cleaved fragments with the restriction enzymes described above were named "pS-1-trp", "pCOP1-1.8-trp" and "pCOP2-1.8-trp", respectively.

EXAMPLE 8

Production of L-Tryptophan by *Brevibacterium flavum* Carrying pCOP1-1.8-trp and pCOP2-1.8-trp, respectively Plasmids pS-1-trp, pCOP1-1.8-trp and pCOP2-1.8-trp prepared in Example 7 were introduced into a strain of *Brevibacterium flavum* (FERM BP-1497). The resulting transformants were named "*Brevibacterium flavum* MJ233-S-trp", "*Brevibacterium flavum* MJ233-COP1-trp" and "*Brevibacterium flavum* MJ233-COP2-trp", respectively.

L-tryptophan was produced by using the three kinds of strains above. In this step, the qualitative analysis of the resulting L-tryptophan was carried out by employing Rf values given by paper chromatography and bioactivity values given by microbiological assay, the quantitative analysis of the resulting L-tryptophan was carried out by using a high performance liquid chromatography ("Shimadzu LC-5A"), and the quantitative analysis of glucose in the reaction solution was carried out by using a glucose analyzer ("GLU-1", available from Toa Denpa Kogyo Kabushiki Kaisha), respectively.

Subsequently, each reaction solution was dividedly introduced into a 500-ml Erlenmeyer flask and sterilized. Then, the solutions, which contained each of said three kinds of strains, was inoculated in the medium A described previously supplemented with chloramphenicol in the final concentration of 6 µg/ml, and glucose was further aseptically added thereto in the final concentration of 5 g/liter. The resulting mixture was cultivated with shaking at 33° C. for 2 days.

One liter of a main culture medium [glucose 5%, ammonium sulfate 2.3% $KH_2PO_4$ 0.05%, $K_2HPO_4$ 0.05%, $MgSO_4.7H_2O$ 0.05%, $FeSO_4.7H_2O$ 20 ppm, $MnSO_4.nH_2O$ 20 ppm, biotin 200 µg/l, thiamin hydrochloride 100 µg/l, Casamino acid 0.3%, yeast extract 0.3%] was charged into a 2 liter jar fermentor, and then sterilized by autoclaving at 120° C. for 20 min. Subsequently, each of the pre-culture liquids described above was added to the medium in a volume of 20 ml, and cultivated for 24 hours under the conditions of a rotation speed of 1000 rpm, an aeration amount of 1 vvm, temperature of 33° C. and pH 7.6.

After completion of the cultivation, 500 ml of the resulting culture liquid was subjected to centrifugation, to harvest cells. The resulting cells were washed twice with deionized water. The washed cells were then suspended in 1000 ml of a reaction solution [$(NH_4)_2SO_4$ 2 g/l, $KH_2PO_4$ 0.5 g/l, $K_2HPO_4$ 0.5 g/l, $MgSO_4.7H_2O$ 0.5 g/l, $FeSO_4.7H_2O$ 20 ppm, $MnSO_4.4-6H_2O$ 20 ppm, thiamin hydrochloride 100 µg/l; pH 7.6]. Then, the resulting solution was charged into a 2 liter jar fermentor, and then 20 g of glucose and 2 g of indole were added thereto. The mixed solution was reacted for 24 hours under the conditions of a rotation speed of 300 rpm, an aeration amount of 0.1 vvm, temperature of 33° C. and pH 7.6.

After completion of the cultivation, the reaction solution was subjected to centrifugation at 4° C. for 15 min at 4000 rpm to give a supernatant. The resulting supernatant was determined for L-tryptophan volumetrically.

The amount of produced L-tryptophan determined for each strain is shown in Table 11 below, as a relative value to the amount of L-tryptophan by produced MJ233-s-trp which being determined as 1.

TABLE 11

| Test strain | Amount of Produced L-tryptophan (Relative value) |
|---|---|
| *Brevibacterium flavum* MJ233-S-trp | 1 |
| *Brevibacterium flavum* MJ233-COP1-trp | 3 |
| *Brevibacterium flavum* MJ233-COP2-trp | 3 |

As shown in Table 11, by using the strains which are transformed with plasmids produced by introducing tryptophan synthase gene into the plasmids pCOP1-1.8 and pCOP2-1.8 exhibiting high copy number of the present invention, L-tryptophan can be produced in higher efficiency than in the conventional methods.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A DNA molecule consisting of the sequence of SEQ. ID. NOS: 7, 9, or 11.

2. A plasmid vector comprising a DNA molecule consisting of the sequence of SEQ. ID. NOS: 7, 9, or 11.

3. A coryneform bacterial host cell transformed with the plasmid vector of claim 2.

4. The coryneform bacterial host cell of claim 3, wherein said bacterial host cell is selected from the group consisting of *Brevibacterium flavum* MJ-233 (FERM BP-1497), *Brevibacterium flavum* MJ-233-AB-41 (FERM BP-1498), *Brevibacterium flavum* MJ-233-ABT-11 (FERM BP-1500), *Brevibacterium flavum* MJ-233-ABD-21 (FERM BP-1499), *Brevibacterium ammoniagenes* ATCC 6871, ATCC 13745, and ATCC 13746, *Brevibacterium devaricatum* ATCC 14020, *Brevibacterium lactofermentum* ATCC 13869 and *Corynebacterium glutamicum* ATCC 31830.

* * * * *